US011266687B2

(12) United States Patent
Mallinson et al.

(10) Patent No.: US 11,266,687 B2
(45) Date of Patent: Mar. 8, 2022

(54) FUNCTIONAL PREDICTION OF CELLULAR FUNCTIONS BY MEANS OF MICRORNA EXPRESSION PROFILING IN MESENCHYMAL STEM CELLS

(71) Applicant: SISTEMIC SCOTLAND LTD, Glasgow (GB)

(72) Inventors: David Mallinson, Glasgow (GB); Donald Dunbar, Glasgow (GB); Elaine Gourlay, Glasgow (GB); Daria Olijnyk, Glasgow (GB); James Reid, Glasgow (GB)

(73) Assignee: SISTEMIC SCOTLAND LTD, Glasgow (GB)

( * ) Notice: Subject to any disclaimer, the term of this patent is extended or adjusted under 35 U.S.C. 154(b) by 365 days.

(21) Appl. No.: 16/300,249

(22) PCT Filed: May 9, 2017

(86) PCT No.: PCT/EP2017/061096
§ 371 (c)(1),
(2) Date: Nov. 9, 2018

(87) PCT Pub. No.: WO2017/194561
PCT Pub. Date: Nov. 16, 2017

(65) Prior Publication Data
US 2019/0160101 A1 May 30, 2019

(30) Foreign Application Priority Data

May 9, 2016 (GB) ..................... 1608081
May 9, 2016 (GB) ..................... 1608086
May 13, 2016 (GB) ..................... 1608497

(51) Int. Cl.
A61K 35/17 (2015.01)
C12Q 1/6883 (2018.01)
A61P 19/00 (2006.01)
A61P 9/00 (2006.01)
A61P 37/06 (2006.01)
A61P 1/00 (2006.01)
A61P 35/00 (2006.01)
C12N 5/0775 (2010.01)
C12N 5/074 (2010.01)
C12Q 1/686 (2018.01)

(52) U.S. Cl.
CPC ............... A61K 35/17 (2013.01); A61P 1/00 (2018.01); A61P 9/00 (2018.01); A61P 19/00 (2018.01); A61P 35/00 (2018.01); A61P 37/06 (2018.01); C12N 5/0663 (2013.01); C12N 5/0696 (2013.01); C12Q 1/686 (2013.01); C12Q 1/6883 (2013.01); C12Q 2600/112 (2013.01); C12Q 2600/158 (2013.01); C12Q 2600/16 (2013.01); C12Q 2600/166 (2013.01); C12Q 2600/178 (2013.01)

(58) Field of Classification Search
CPC ..................................................... A61K 35/17
See application file for complete search history.

(56) References Cited

FOREIGN PATENT DOCUMENTS

| WO | 2012025709 A1 | 3/2012 | |
| WO | WO2012/025709 | * 3/2012 | ............. A61K 35/17 |
| WO | 2014024183 A1 | 2/2014 | |
| WO | 2015051210 A1 | 4/2015 | |
| WO | 2015157678 A2 | 10/2015 | |

OTHER PUBLICATIONS

Tocci et al. (The Hematology Journal. 2003; 4:92-96) (Year: 2003).*
Chi et al. (Molecular Medicine Reports 14: 4187-4197, 2016) (Year: 2016).*
Benjamini, Y. et al., "Controlling the False Discovery Rate: A Practical and Powerful Approach to Multiple Testing", Journal of the Royal Statistical Society. Series B (Methodological), 1995, pp. 289-300, vol. 57, No. 1, © 1995 Royal Statistical Society.
Gentleman, R.C. et al., "Bioconductor: open software development for computational biology and bioinformatics", Genome Biology, Sep. 15, 2004, pp. R80.1-R80.16, vol. 5, No. 10, Article R80, © 2004 Gentleman et al.
Roubelakis, M. et al., "Identification and Functional Analysis of Novel miRNA Target Genes That Control Mesenchymal Stem Cell Function", Blood, 2008, Abstract, p. 2424, vol. 112, No. 11; http://www.bloodjournal.org/content/112/11/2424.
Han, J. et al., "Specific microRNA expression during chondrogenesis of human mesenchymal stem cells", International Journal of Molecular Medicine, 2010, pp. 377-384, vol. 25; DOI: 10.3892/ijmm_00000355.
Camarillo, C. et al., "Comparison of microarray and quantitative real-time PCR methods for measuring microRNA levels in MSC cultures", Methods Mol. Biol., 2011, pp. 419-429, vol. 698, Author Manuscript available in PMC May 25, 2015, 10 pages; DOI: 10.1007/978-1-60761-999-4_30.
Lopez-Romero, P., "Pre-processing and differential expression analysis of Agilent microRNA arrays using the AgiMicroRna Bioconductor library", BMC Genomics, 2011, 8 pages, vol. 12, No. 64, ©2011 López-Romero.
Eskildsen, T. et al., "MicroRNA-138 regulates osteogenic differentiation of human stromal (mesenchymal) stem cells in vivo", PNAS, 2011, 6 pages, vol. 108, No. 15; DOI: 10.1073/pnas.1016758108.

(Continued)

Primary Examiner — Scott Long
(74) Attorney, Agent, or Firm — Blue Filament Law PLLC

(57) ABSTRACT

Non-coding RNA, such as miRNA, expression data derived from a cell population is used to infer the propensity of that cell population for a cellular functional effect for a predetermined purpose, which effect is temporally, procedurally or interventionally separated from the cell population from which the expression data is derived. Thereby, the cellular functional effect of a cell population can be predicted in order to improve decisions and selections to be made relating to the use of cells, e.g. from cells deriving from different donors or batches, for use in bioprocess application or cell therapeutics, in order to enhance productivity, efficiency and/or efficacy.

11 Claims, 5 Drawing Sheets

(56) References Cited

OTHER PUBLICATIONS

Zhang, J.F. et al., "MiRNA-20a promotes osteogenic differentiation of human mesenchymal stem cells by co-regulating BMP signaling", RNA Biology, Sep./Oct. 2011 (Published Online: Jul. 28, 2011), pp. 829-838, vol. 8, No. 5, ©2011 Landes Bioscience; DOI: 10.4161/rna.8.5.16043.

Liu, L. et al., "MicroRNA-181a Regulates Local Immune Balance by Inhibiting Proliferation and Immunosuppressive Properties of Mesenchymal Stem Cells", Stem Cells, Jun. 19, 2012, 26 pages, vol. 30, No. 8, © 2018 AlphaMed Press; DOI: 10.1002/stem.1156.

Zhang, R. et al., "The role of microRNAs in adipocyte differentiation", Front. Med., 2013, 8 pages, vol. 7, No. 2, © Higher Education Press and Springer Verlag Berlin Heidelberg 2013; DOI: 10.1007/s11684-013-0252-8.

Chen, K.D. et al., "Identification of miR-27b as a Novel Signature from the mRNA Profiles of Adipose-Derived Mesenchymal Stem Cells Involved in the Tolerogenic Response", PLOS One, Apr. 16, 2013, 14 pages, vol. 8, No. 4, e60492, © 2013 Chen et al.; DOI: 10.1371/journal.pone.0060492.

Huang, F. et al., "Overexpression of miR-126 promotes the differentiation of mesenchymal stem cells toward endothelial cells via activation of PI3K/Akt and MAPK/ERK pathways and release of paracrine factors", Biological Chemistry, Published Online: May 29, 2013, pp. 1223-1233, vol. 394, No. 9; DOI: 10.1515/hsz-2013-0107.

Zhao, X. et al., "Circulating MIR-586 Participates in Occurrence of Acute Graft-Versus-Host-Disease by Down-Regulating Indoleamine-2,3-Dioxygenase", Abstract, Haematologica, 19th Congress of the European Hematology Association, Milan, Italy, Jun. 12-15, 2014, Abstract Book, vol. 99, Supplement No. 1, 2014 | s1, S1365, p. 535, © 2014 by Ferrata-Storti Foundation/European Hematology Association.

Zhao, X. et al., "Circulating Mir-153 Participates in Occurrence of Acute Graft-Versus-Host Disease by Down-Regulating Indoleamine-2,3-Dioxygenase", Abstract, Blood, 2014, vol. 124, No. 21, p. 2428, © 2014 by the American Society of Hematology; http://www.bloodjournal.org/content/124/21/2428.

Gunel-Ozcan, A. et al., "miRNA Expression Profiling in Mesenchymal Stromal/Stem Cells Derived from G-CSF Primed Bone Marrows", Abstract, Blood, 2014, vol. 124, No. 21, p. 5140, ©2014 by the American Society of Hematology; http://www.bloodjournal.org/content/124/21/5140.

Zhao, G. et al., "Differential expression of microRNAs in decidua-derived mesenchymal stem cells from patients with pre-eclampsia", Journal of Biomedical Science, 2014, 12 pages, vol. 21, No. 81, ©2014 Zhao et al.; DOI: 10.1186/s12929-014-0081-3.

Li, W. et al., "Immunomodulatory Effects of Bone Marrow-Derived Mesenchymal Stem Cells on Pro-Inflammatory Cytokine-Stimulated Human Corneal Epithelial Cells", PLOS One, Jul. 8, 2014, 12 pages, vol. 9, No. 7, e101841, β 2014 Wen et al.; DOI: 10.1371/journal.pone.0101841.

Oikonomopoulos, A. et al., "Inhibition of microRNA-29a in Human Bone Marrow Mesenchymal Stem Cells Increases Their Immunomodulatory Function", Gastroenterology, 2015, Abstract, Mo1837, p. S-723, vol. 148, No. 4.

Oikonomopoulos, A. et al., "IFN-γ Regulates the Immunosuppressive Properties of Bone Marrow Mesenchymal Stem Cells in a microRNA-29a/STAT-3 Dependent Manner", Gastroenterology, 2016, Abstract, Sa1730, p. S-359, vol. 150, No. 4.

Search Report dated Jan. 5, 2017 for UK Application No. GB1608081.4 filed May 9, 2016.

Search Report dated Jan. 17, 2017 for UK Application No. GB1608086.3 filed May 9, 2016.

International Search Report dated Jul. 11, 2017 for International Application No. PCT/EP2017/061096 filed May 9, 2017.

\* cited by examiner

FUNCTIONAL PREDICTION OF CELLULAR FUNCTIONS BY MEANS OF MICRORNA EXPRESSION PROFILING IN MESENCHYMAL STEM CELLS

FIELD OF THE INVENTION

This invention pertains generally to the predictability of cellular function. More particularly, the invention relates to the prediction functional outcome in the application of cell populations to a purpose such as cell therapy.

BACKGROUND OF THE INVENTION

Many biological and clinical processes are facilitated by the application of cells. Cell therapy (such as stem cell therapy) in particular has clinical utility and is showing tremendous promise for a range of indications by a range cell therapy approaches.

Cell therapies (and other bioprocessing uses of cells) suffer from variability in performance and predictability due to the variability of phenotype and characteristics of both sources of cells and target tissues (e.g. in prospective patients). This results, potentially, in efficacy as well as cost and efficiency being considerably affected and in some cases affects the viability of the application.

It would be of enormous benefit to be able to predict functional outcomes in order to make selection decisions— e.g. therapeutic choices, donor selection or batch selection.

MicroRNAs (miRNA) are single-stranded RNA molecules having a length of around 21 to 23 nucleotides which regulate gene expression in cells at the translational level. Within a cell, a single miRNA can regulate multiple genes and each gene can be regulated by multiple miRNAs. There are currently 2588 known human miRNAs. MiRNA are known to provide useful biomarkers for disease. It is known that miRNAs can be used to characterize cells and can be used to monitor when cells have changed (e.g. phenotypic changes), or have differentiated, as discussed in WO-A-2012/025709.

The present inventors have identified that microRNA (miRNA) profile data can be used to predict a wide range of functional outcomes in biological systems.

Problem to be Solved by the Invention

There is a need for improvements in the predictability of functional outcome in cell applications in biological systems and for making selection decisions.

It is an object of this invention to provide a method for predicting the functional outcome the application of cells or interventions on cells in a biological system.

It is a further object of this invention to provide an assay for use in gathering data upon which to make a prediction of functional outcome and/or make a selection of materials for use according to the prediction of functional outcome.

It is a further object of this invention to provide a method for selection of donor cells or cell batches based on a functional outcome from the use of those cells.

SUMMARY OF THE INVENTION

In accordance with a first aspect of the invention, there is provided a use of non-coding RNA (or miRNA) expression data or expression profiles to identify, determine or infer propensity for, or to predict, a cellular functional effect for a pre-determined purpose.

In a second aspect of the invention, there is provided a method of identifying, determining or inferring propensity for (or predicting) a cellular functional effect for a pre-determined purpose, the method comprising assaying against a pre-determined non-coding RNA (or miRNA) or panel of non-coding RNAs (or miRNAs) the expression of which is known or determined to correlate with the cellular functional effect, generating non-coding RNA (or miRNA) expression data for the assayed non-coding RNA (or miRNA) or panel of non-coding RNAs (or miRNAs) and from the non-coding RNA (or miRNA) expression data identifying, determining or inferring a propensity for the cellular functional effect. For example, this is typically by comparing the expression data from the assay with expression levels (actual, e.g. ranges or thresholds, or relative), trends or patterns known to be associated with cellular functional effect.

In a third aspect of this invention, there is provided a method of applying a cell population to a pre-determined purpose, the method comprising inferring a cellular function effect for the predetermined purpose by the method defined above and applying the cell population for the pre-determined purpose.

In a fourth aspect of this invention, there is provided a method for screening populations of donor-derived cells (e.g. stem cells such as MSCs) for use in treatment of an indication or condition or for further manipulation for later treatment of an indication or conditions, the method comprising inferring a cellular function effect pertinent to the treatment of the indication or the further manipulation and in dependence of that inference, selecting populations of donor-derived cells (or selecting donors for further donation of cells) for use in the treatment of the indication or the further manipulation.

In a fifth aspect of this invention, there is provided a method for determining the dose of a population of cells (e.g. stem cells, such as MSCs or T-cells) for administration to a patient for treating a condition which depends upon a cellular functional effect, the method comprising measuring a non-coding RNA (or miRNA) expression profile for the cells for a pre-determined non-coding RNA (or miRNA) or panel of non-coding RNAs (or miRNAs) known to correlate with the cellular functional effect and inferring therefrom a relative propensity to the cellular functional effect and determining therefrom with reference, for example, to a predetermined dose for a pre-determined propensity to the cellular functional effect an actual dose to be administered to a patient.

In a sixth aspect of this invention, there is provided a method of treatment of a human or animal patient in need thereof, the method comprising administering one or a plurality of cell therapy doses to said patient, said cell therapy dose effective in treating said patient by a cellular function effect as between the cell therapy and the patient, the cellular function effect having been inferred by use of non-coding RNA (or miRNA) expression profile.

In a seventh aspect of this invention, there is provided a population of cells selected to have a non-coding (or miRNA) expression profile for a pre-defined non-coding RNA (or miRNA) or panel of non-coding RNAs (or miRNAs) that correlates with a pre-defined cellular functional effect optionally for a pre-determined purpose.

In an eighth aspect of this invention, there is provided a cell population for use in the treatment of a condition in a patient in need thereof, which treatment is mediated by a pre-defined cellular functional effect, the cell population provided in a dose or dosage regimen determined according to the non-coding RNA (or miRNA) expression of the cell population for a pre-defined non-coding RNA (or miRNA) or panel of non-coding RNAs (or miRNAs) that correlates with the cellular functional effect to a degree that corresponds with one of a plurality of possible doses or dosage regimen.

In a ninth aspect of the invention, there is provided a kit for use to identify, determine or infer the propensity or relative propensity of a population of cells for a cellular functional effect, optionally for use in a pre-determine purpose, the kit comprising primers for use in quantitative PCR (polymerase chain reaction), primers being for a non-coding RNA (or miRNA) or panel of non-coding RNAs (or miRNAs) known or identified as correlating with the cellular functional effect.

In a tenth aspect of the invention, there is provided a method of identifying or determining one or more non-coding RNA (or miRNA) the expression of which in the cell population being assayed is correlating with a cellular functional effect of the cell population (e.g. when administered, subject to an intervention or treated), preferably for a predetermined purpose, for use of said one or more non-coding RNAs (or miRNAs) in a panel for identifying, determining or inferring the cellular functional effect, the method comprising:

Sourcing cell populations intended for effecting the cellular functional effect from multiple sources (e.g. multiple donors or multiple production batches of different provenance);

Treating and using a first sample of each cell population to isolate total RNA for non-coding (or miRNA) expression profiling thereby generating an extensive non-coding RNA expression profile data set for each cell population [or preferably a miRNA expression profile data set for each cell population (e.g. based on at least 100 miRNAs, preferably at least 800, more preferably at least 1000 and most preferably at least 2000 miRNAs)];

Subjecting a second sample of each cell population to an intervention designed to elicit a cellular functional effect and the extent of the cellular functional effect monitored by a known or conventional or surrogate means to generate 'response data';

Correlating the extensive non-coding (or miRNA) expression profile data set with response data for each cell population;

Identifying correlating non-coding RNA (or miRNA), preferably that correlate positively or negatively with a correlation coefficient of at least 7 or at least 8; and selecting such correlating non-coding RNA (or miRNA) as candidates for a miRNA expression panel for the cellular functional effect.

Advantages of the Invention

Figure 1:
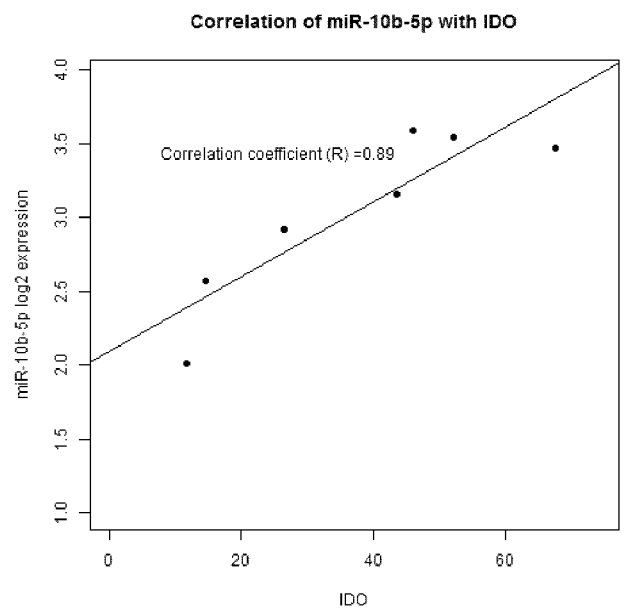
FIG. 1 is a correlation plot of miR-10b-5p expression levels vs IDO-induction.
Figure 2:
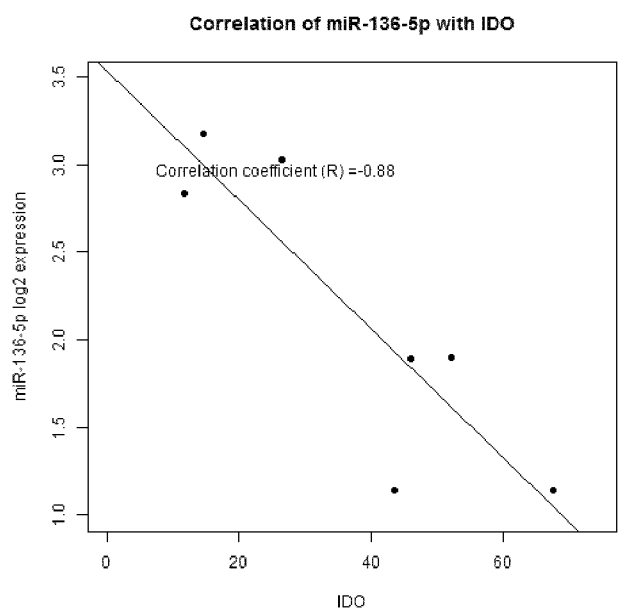
FIG. 2 is a correlation plot of miR-136-5p expression levels vs IDO-induction.
Figure 3:
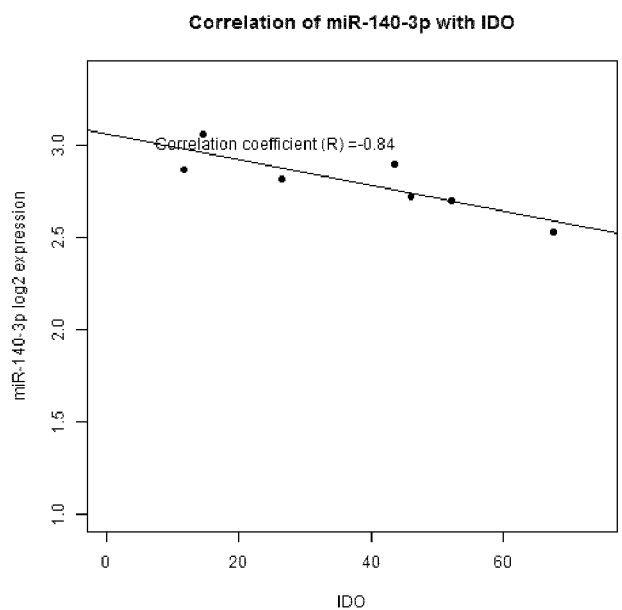
FIG. 3 is a correlation plot of miR-140-3p expression levels vs IDO-induction.
Figure 4:
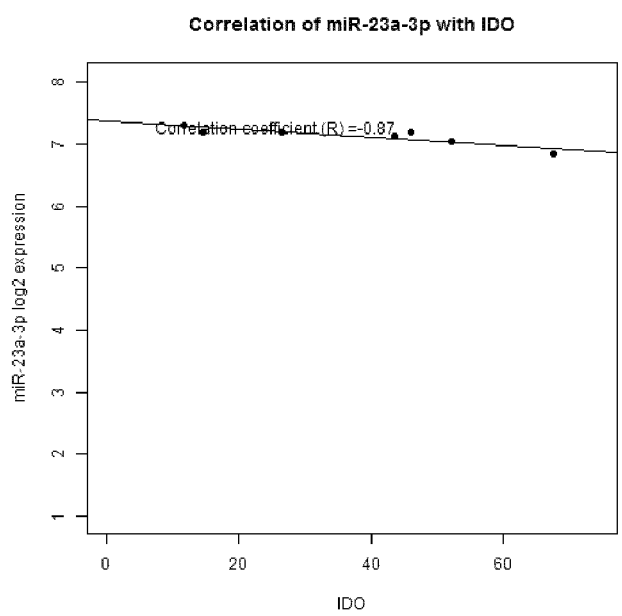
FIG. 4 is a correlation plot of miR-23a-3p expression levels vs IDO-induction.
Figure 5:
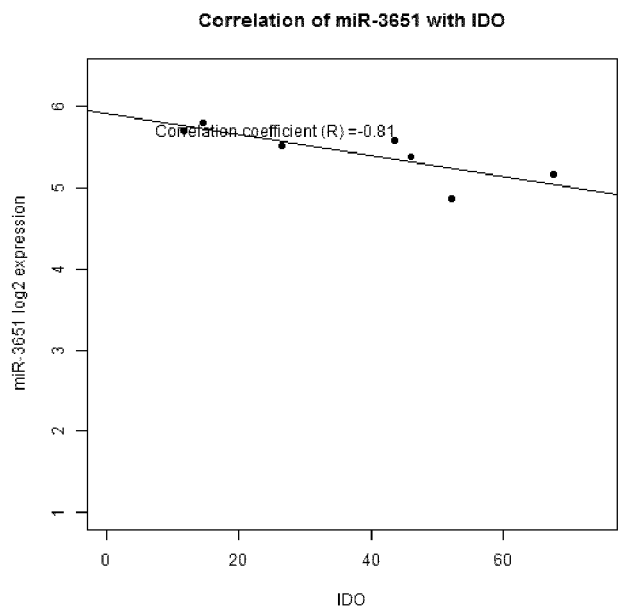
FIG. 5 is a correlation plot of miR-3651 expression levels vs IDO-induction.
Figure 6:
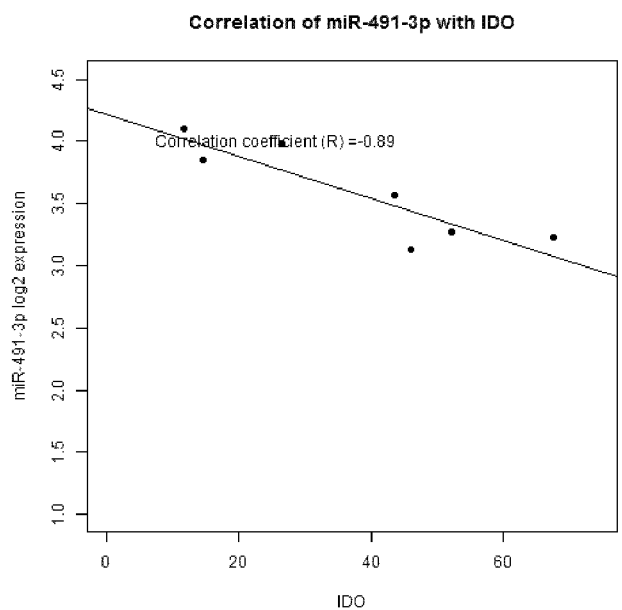
FIG. 6 is a correlation plot of miR-491-3p expression levels vs IDO-induction.
Figure 7:
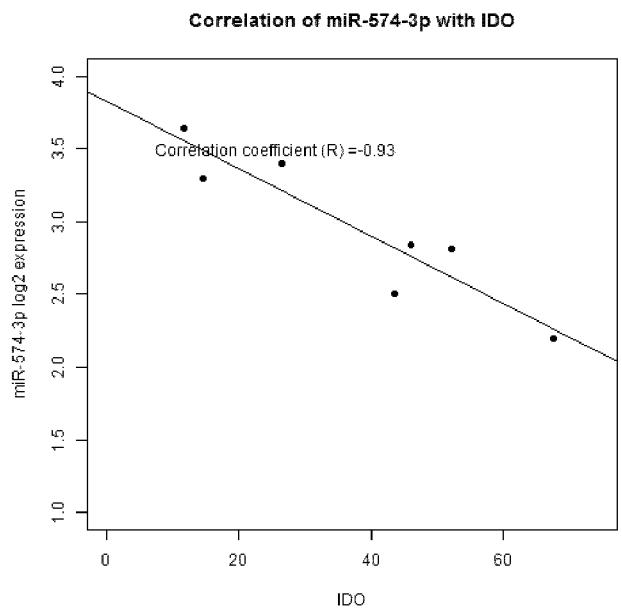
FIG. 7 is a correlation plot of miR-574-3p expression levels vs IDO-induction.
Figure 8:
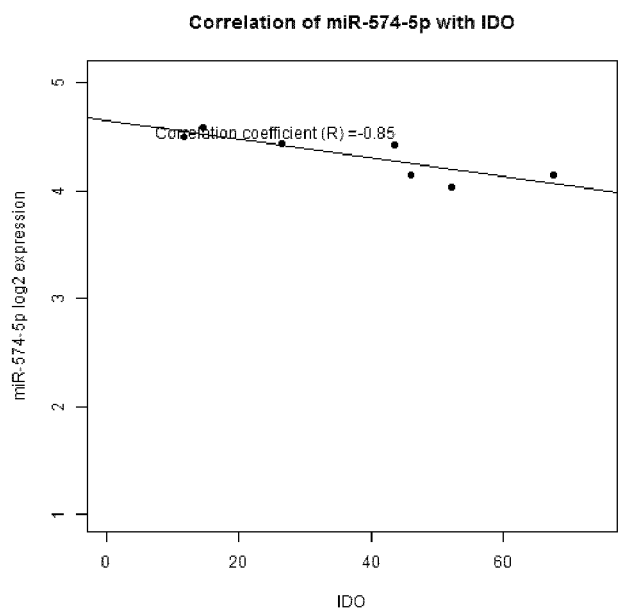
FIG. 8 is a correlation plot of miR-574-5p expression levels vs IDO-induction.

The use and method of the present invention enables decision to be made and selections to be made relating to the use of cells, e.g. from particular or categories of donors or batches, in bioprocess applications or cell therapeutics that enhance efficiency and/or efficacy. In particular, in cell therapy, the method enables the decisions and selection in relation to cell populations for the development of application of a cell therapy for a patient with improved efficacy and efficiency.

DETAILED DESCRIPTION OF THE INVENTION

The invention concerns the use of non-coding expression data or expression profiles to identify, determine or infer propensity for a cellular functional effect, preferably for a pre-determined purpose. The use can be effected, for example, by assaying against a pre-determined non-coding RNA or panel of non-coding RNA, the expression of which is already identified as correlated with the cellular functional effect or a known surrogate or assay or other process associated with the cellular functional effect. Preferably, the panel of non-coding RNA comprises at least two non-coding RNA and preferably up to six non-coding RNA.

The term 'non-coding RNA' may include miRNA (microRNA) or other non-coding RNA. The term 'non-coding RNA' typically refers to RNAs that do not encode a protein and generally encompass classes of small regulatory RNAs. Other non-coding RNAs referred to above may be, for example, small interfering RNA (siRNA), piwi-interacting RNA (pi RNA), small nuclear RNA (snRNA), small nucleolar RNA (snoRNA), extracellular RNA (exRNA), Small Cajal body RNA (scaRNA) and short hairpin RNA (shRNA). Other non-coding RNAs may further comprise transgenic non-coding RNAs which may function as reporters of non-coding RNA expression. Other non-coding RNAs may be episomal and the methods and/or uses described may require initial steps in which episomal DNA is introduced into the cells described herein whereupon the episomal DNA can be transcribed to produce non-coding RNA which constitutes all or part of the profiled non-coding RNA. In one embodiment, the term non-coding RNA does not include non-coding RNAs known as teloRNA.

The term miRNA (microRNA) may include miRNA molecules and either or both miRNA precursors and mature miRNAs as is apparent from the context, but are preferably mature miRNAs.

Hereinafter, embodiments of the invention (and further aspects) will be described by reference to miRNAs. Optionally as an alternative to any or all of the embodiments of the invention described hereinafter, the references to miRNA may instead be to non-coding RNA or other non-coding RNA (such as those defied above) where the context allows (e.g. other than when referring to specific miRNAs).

Preferably, the invention is directed to the use of miRNA expression data or expression profiles to identify, determine or infer propensity for a cellular functional effect, preferably for a pre-determined purpose. The use can be effected, for example, by assaying against a pre-determined miRNA or panel of miRNA, the expression of which is already identified as correlated with the cellular functional effect or a known surrogate or assay or other process associated with the cellular functional effect. Preferably, the panel of miRNA comprises at least two miRNA and preferably up to six miRNA.

The miRNA expression data or expression profile is preferably expression data for a miRNA or panel of miRNAs known or determined as having expression, expression levels or an expression profile correlating with the cellular functional effect (or known surrogate or assay or marker for or associated with the cellular functional effect). The expression, expression level or expression profile may be correlated positively or negatively with the cellular functional effect.

The miRNA expression data may be expression data for at least one miRNA, preferably at least two and more preferably up to six miRNAs having a pre-determined correlating effect with the cellular functional effect and preferably wherein at least one miRNA is positively correlated and at least one miRNA is negatively correlated with the cellular functional effect.

A cellular functional effect is any functional effect of a cell or by a cell and is preferably associated with a functional outcome. A cellular functional effect is typically an effect that is potentially variable due, for example, to phenotypic differences between cells or cell populations from different sources (e.g. in different donors or patients) that may not readily determinable until after the application or use or by carrying out an assay or test for the effect or a surrogate marker. Preferably, the cellular functional effect is a functional effect of a cell to be used for a further or pre-determined use and preferably the cellular functional effect is not demonstrable until after the cell has been put to that further or pre-determined use. Given that with cell therapies or other cell applications (such as bioprocess applications), the timeframe and cost of expanding cell populations or securing donations of cells for use in cell therapy (or bioprocess development) is significant, it is a significant impediment to cost effective therapy or use (e.g. in bioprocess production) and effective further use (e.g. effective therapy for the patient) to have variable or poor cellular functional effects or functional outcomes. The use of miRNA expression data or profiles and panels of miRNA in assays in accordance with the present invention addresses the problems with variable or unpredictable cellular functional effects and functional outcomes. A functional outcome may be considered the result of the cellular functional effect in the context of a pre-determined purpose.

A pre-determined purpose is preferably the purpose or use that the cellular functional effect has or is associated with. Typically, the effectiveness for the predetermined purpose is dependent upon the cellular functional effect. The pre-determined purpose may be any suitable purpose such as bioprocess applications, regenerative medicine, cell therapy, patient stratification (e.g. for cell or other therapy), cell growth or donor selection for example.

By way of an example, a cellular functional effect may be the migration potential of CD34+ cells toward SDF-1 or the IDO induction activity of a population of MSCs, a functional outcome may be respectively engraftment potential of CD34+ cells or immunosuppressive activity of MSCs and a pre-determined purpose may be respectively determination of dose for CD34+ for autologous therapy or donor selection for, dose determination for or therapy by T-cell suppression therapy (e.g. for Graft vs Host Disease).

The invention further comprises a method of identifying, determining or inferring propensity for a cellular functional effect for a pre-determined purpose, the method comprising assaying, for example tissue or cells or cell populations, against a pre-determined miRNA or panel of miRNAs known or determined to correlate with the cellular functional effect, generating miRNA expression data for the assayed miRNA or panel of miRNAs and identifying, determining or inferring therefrom a propensity for the cellular functional effect. This may be achieved by comparing the expression data generated from the assay with expression levels (actual, e.g. ranges or thresholds, or relative), trends or patterns known to be associated (or correlated) with cellular functional effect and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with the cellular functional effect. Preferably, a selection or decision may be made to provide an enhanced functional outcome or enhanced efficacy of the pre-determined purpose based on the determined propensity (or relative propensity) for the cellular functional effect. That selection may be, for example, the selection of cell populations that meet or exceed a pre-determined threshold of propensity for the cellular functional effect for use in the pre-determined purpose or the selection of donors (as individuals or determined donor groups determined or inferred to have a similar characteristic) for donation of cells for a further use. That selection may be, for example, the selection of those cell populations that better demonstrate propensity for the cellular functional effect (that is, have a better relative propensity) for use in the pre-determined purpose.

Optionally, the expression levels or patterns (or degree of correspondence or correlation) of the miRNA expression data may be validated against the functional outcome of the cellular functional effect in order to attribute an absolute value (e.g. a threshold) or a scale to the miRNA expression data or correlation thereof with the cellular functional effect or functional outcome from which a precise prediction or inference can be derived and thereby a decision or selection may optionally be made.

The invention further comprises a method of applying a cell population to a pre-determined purpose, the method comprising inferring (or determining) a cellular function effect for the predetermined purpose by the method defined above and in dependence of the inference (or determination) applying the cell population for the pre-determined purpose.

The invention further comprises a method of identifying or determining one or more miRNA correlating with a cellular functional effect, preferably for a predetermined purpose, for use in a panel of miRNA for inferring a cellular functional effect.

The invention further comprises the use of a panel of miRNA (or miRNA adapted for assay form) in an assay for inferring a cellular functional effect for which panel of miRNA the expression has been determined as correlating with a cellular functional effect.

The invention further comprises a kit for use in inferring a cellular function effect for use in a pre-determined purpose. The kit may comprise a panel of miRNAs (or equivalent reagents in a form suitable for an assay) and optionally a protocol and method for an assay and optionally a database or dataset relating to an indication of expression levels (e.g.

thresholds or ranges) or patterns of miRNA associated with pre-defined and optionally validated expression levels. The kit may typically be for use in PCR (polymerase chain reaction), typically quantitative PCR and comprise primers for a miRNA or panel of miRNAs.

In one embodiment, the pre-determined purpose is cell therapy (for example stem cell therapy). According to this embodiment, the invention further comprises a method of treatment of a human or animal patient in need thereof, the method comprising administering one or a plurality of cell therapy doses to said patient, said cell therapy dose effective in treating said patient by a cellular functional effect as between the cell therapy and the patient, the cellular functional effect having been determined or inferred by use of miRNA expression profile, preferably by assaying against miRNAs known or determined to be correlated with the cellular functional effect.

In another embodiment, the pre-determined purpose is a bioprocess application, for example the production of a protein (e.g. protein-based therapeutics such as monoclonal antibodies) from cultures cells (e.g. murine myeloma cells, Chinese hamster ovary cells, baby hamster kidney cells or human embryonic kidney cells). The invention according to this embodiment is directed to identifying, determining or inferring (or predicting) the productivity of cells in producing the required molecules or protein therapeutics and optionally selecting cells (e.g. cell populations or cell batches, or cell lines or strains) for such uses in dependence of their predicted productivity.

The term cell or cell population should be understood to encompass any eukaryotic cell. For example a cell or cell population may be or comprise a mammalian (adult, foetal or embryonic) and preferably a human cell including, for example, T-cells, progenitor cells (e.g. tissue-specific progenitor cells, their intermediates stages differentiating to one or more terminal states) or stem cells. The stem cells may be, for example, cell populations comprising embryonic stem cells, induced pluripotent stem cells, haematopoietic stem cells (e.g. CD34+ cells) or mesenchymal stem/stromal cells.

The present invention in its broadest sense comprises at least two general embodiments.

In a first general embodiment, it concerns use of miRNA expression data of a cell, cell population or cell sample (together referred to as cells hereafter) preferably for further use or for use in a pre-determined purpose, to identify, determine or infer propensity for a cellular functional effect associated with the pre-determined purpose.

The use preferably is by assaying cells against a pre-determined miRNA or panel of miRNA, the expression of which is already identified as associated or correlated with the cellular functional effect or a known surrogate or assay or other process associated with the cellular functional effect. The panel of miRNA may comprise any number of miRNA (e.g. one or more), the expression of which are typically correlated with the cellular functional effect (or another assay or process considered equivalent to the cellular functional effect) and may be positively or negatively correlated or may comprise one or more miRNA positively correlated with the cellular functional effect and/or one or more miRNA negatively correlated with the cellular functional effect. Preferably, the panel of miRNA comprises at least two miRNAs and preferably up to six miRNAs.

By expression data, it is meant expression levels, relative expression levels or expression profiles or patterns of miRNA of the cells.

The miRNA expression data is preferably expression data for a miRNA or panel of miRNAs of the cells, the miRNA or panel of miRNAs known or determined as having expression, expression levels or an expression profile correlating with the cellular functional effect (or known surrogate or assay or assay or marker for or associated with the cellular functional effect).

Preferably, the miRNA expression data is expression data for two to six miRNAs having a pre-determined correlating effect with the cellular functional effect and preferably wherein at least one miRNA is positively correlated and at least one miRNA is negatively correlated with the cellular functional effect.

The cellular functional effect according to this general embodiment is a functional effect of a cell to be used for a further or pre-determined use which cellular functional effect is typically not readily demonstrable in the cells until after the cell has been put to that further or pre-determined use or by some other assay of the cells. Preferably, cellular functional effect can be said to be a characteristic of the manner in which cells interact at a cellular level in vivo or in vitro (according to the pre-determined purpose).

A cellular functional effect is preferably a functional effect of a cell or cell population or functional outcome of application of the cell or cell population for a purpose, which effect is separated temporally, procedurally or interventionally from the cells or cell population from which the inference or identification is being made (by means of assaying for miRNA expression).

The cellular functional effect may be demonstrable a period of time after the assay for inferring or identifying propensity for the cellular functional effect, for example due to phenotypic changes that the cell population may be pre-disposed to. Alternatively, the cellular functional effect may be demonstrable upon a process or procedure being applied to the cell population. Alternatively the cellular functional effect may demonstrable after an intervention performed on the cell population. Such an intervention or procedural step may cause or induce a change in phenotype or induce a particular effect. For example, the intervention or procedural step may be an intervention to induce expression or an assay to determine an effect or to induce an effect. The intervention or procedural step may be a tagging step. The intervention may be the in vitro culture of the cell population, optionally under certain conditions, or serial passages (e.g. 5, 10, 20, 40 or 80 passages) of a population of cells in in vitro culture. The intervention or procedure step may comprise administering the cell population to a patient (i.e. applying it to an in vivo environment) optionally in combination with another intervention. In broad terms, an intervention may be, for example, any intervention which may be applied to or which acts on a cell and which potentially may cause phenotypic changes or altered function. Further examples of interventions may include the application of one or more test agent to the cell population, either simultaneously or sequentially, which one or more test agent may be a chemical entity, for example, a molecule having a molecular weight of less than 2,000 Daltons, less than 1,000 Daltons or less than 500 Daltons, or non-polymeric, or a biological entity (e.g. a biological macromolecule, such as a lipid, an oligonucleotide, or a protein such as an enzyme, an antibody, or antibody fragment, humanized antibody or antibody fragment, phage or ribosome displayed protein fragment, or a prion, or a virus or bacteria). Such a test agent intervention may be a therapeutic agent. An intervention may comprise the application to a cell population of one or more of a group comprising: ionising radiation, continuously emitted or pulsed electromagnetic radiation (for example, visible light, ultra-violet light, infra-red light), acoustic energy (delivered through air or through a liquid medium), mechanical intervention (for example, the application of pressure), electricity, changes in temperature, changes in the osmolarity, tonicity or pH of a growth medium, magnetic fields, changes in fluid dynamics, and mechanochemical signal transduction. An intervention may be one that can potentially cause a change in the differentiation or de-differentiation state of a stem cell or progenitor cell, or which causes a stem cell or progenitor cell to specialize, or to replicate while maintaining the characteristics of a particular cell lineage or differentiation state.

Preferably, the cellular functional effect, the propensity for which a population of cells is identified, determined or inferred as having according to an aspect of the present invention, in dependence upon non-coding or miRNA expression data or an expression profile (the predictive data or predictive profile) derived from the population of cells, is not contemporaneous with the predictive data or predictive profile. Preferably, the cellular functional effect is separated in time from the predictive data or predictive profile, by which it is meant from time at which the predictive data or predictive profile is derived from a population of cells or sample thereof. The separation in time may be any suitable time such as at least 15 minutes, at least an hour, at least 24 hours, at least 1 week or at least 1 month. This non-contemporaneous nature may be better defined in terms of cell passages, e.g. separated by at least one passage, at least two passages, at least 6 passages or at least 12 passages.

Optionally, according to an embodiment of the present invention, the cellular functional effect is not demonstrable in the cell population from which the non-coding RNA or miRNA expression data or profile derives (at the time a sample is taken for deriving such expression data or profile), but only after a passage of time, application of a process or procedure, or of an intervention on the cell population.

In a preferred embodiment of the use and method of the invention, non-coding RNA or miRNA expression data or expression profile may be derived from a population of cells (e.g. a first population of cells) at a first occasion for use in identifying, determining or inferring the propensity for a cellular functional effect in a population of cells (e.g. a second population of cells) at a second occasion. The second occasion and first occasion are typically separated temporally, by process or by intervention on the cell population. The second population of cells preferably derives from the first population of cells by the passage of time, application of a process or an intervention on the first population of cell.

It is a preferred embodiment of the invention that the use and method is for predicting a cellular functional effect (and optionally a functional outcome) in a population of cells that is to be subject to a passage of time, application of a process or procedure or subject to an intervention and in particular to predict the cellular functional effect (or identify, determine or infer the propensity thereof) in a population of cells after a passage of time, application of a process or procedure or after an intervention, based upon non-coding RNA or miRNA expression data or expression profiles derived from the population of cells before the passage of time, the application of the process or procedure or before the intervention.

The use according to this embodiment is preferably intended to enable prediction, determination or inference as to propensity of cells to a cellular functional effect leading to a functional outcome for use in a pre-determined purpose. Preferably, this is in order to make a selection (e.g. of cells from cell samples or populations of nominally the same category or type but having differing provenance, such as differing donor, differing storage conditions or differing process or treatment conditions, to use selected cells for a pre-determined purpose) or decision (e.g. to proceed with a cellular therapy or not based on an absolute determination of propensity or to determine quantity of cells to be used for expansion or to determine doses for administration to a cell therapy patient).

A pre-determined purpose according to this general embodiment is a purpose or use of the cells that the cellular functional effect has or is associated with. The pre-determined purpose may be any purpose to which cells can be put which rely on some functional effect of the cells (and a functional outcome of applying the cells). The pre-determined purpose may be, for example, a bioprocess application, a regenerative medicine application, cell therapy, cell growth or donor selection.

The invention according to this general embodiment further comprises a method of identifying, determining or inferring propensity of cells for a cellular functional effect for a pre-determined purpose, the method comprising assaying cells against a pre-determined miRNA or panel of miRNAs known or determined to correlate with the cellular functional effect, generating miRNA expression data of the cells for the assayed miRNA or panel of miRNAs and identifying, determining or inferring therefrom the a propensity of the cells for the cellular functional effect. This may be achieved by comparing the expression data generated from the assay with expression levels (actual, e.g. ranges or thresholds, or relative), trends or patterns known to be associated (or correlated) with cellular functional effect and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with the cellular functional effect. Preferably, a selection or decision may be made to provide an enhanced functional outcome or enhanced efficacy of the pre-determined purpose based on the determined propensity (or relative propensity) of the cells for the cellular functional effect. That selection may be, for example, the selection of cell populations that meet or exceed a pre-determined threshold of propensity for the cellular functional effect for use in the pre-determined purpose or the selection of donors (as individuals or determined donor groups determined or inferred to have a similar characteristic) for donation of cells for a further use. That selection may be, for example, the selection of those cell populations that better demonstrate propensity for the cellular functional effect (that is, have a better relative propensity) for use in the pre-determined purpose.

Optionally, the expression levels or patterns (or degree of correlation) of the miRNA expression data may be validated against the functional outcome of the cellular functional effect in order to attribute an absolute value (e.g. a threshold) or a scale to the miRNA expression data or correlation thereof with the cellular functional effect or functional outcome from which a precise prediction or inference can be derived and thereby a decision or selection may optionally be made.

The invention according to this general embodiment further comprises a method of identifying or determining one or more miRNA the expression of which in the cell population being assayed is correlating with a cellular functional effect of the cell population (e.g. when administered, subject to an intervention or treated), preferably for a predetermined purpose, for use of said one or more miRNAs in a panel for identifying, determining or inferring the cellular functional effect. The method preferably comprises:

Sourcing cell populations intended for effecting the cellular functional effect from multiple sources (e.g. multiple donors or multiple production batches of different provenance);

Treating and using a first sample of each cell population to isolate total RNA for miRNA expression profiling (e.g. using Agilent miRNA microarrays: one version of which, Agilent MiRBase version 16, contains 1199 human miRNAs; and another version of which, Agilent MiRBase version 21, contains 2549 human miRNAs) thereby generating an extensive (e.g. based on at least 100 miRNAs, preferably at least 800, more preferably at least 1000 and most preferably at least 2000 miRNAs) miRNA expression profile data set for each cell population;

Subjecting a second sample of each cell population to an intervention designed to elicit a cellular functional effect (said intervention being, for example, administration to a patient with a target indication, treating with an agent the response to which is to be predicted, subjecting to an in vitro assay against something, subjecting to an inducing environment such as to induce proliferation or to induce differentiation into one or another differentiate, or expanding to assess proliferation rate) and the extent of the cellular functional effect monitored by a known or conventional or surrogate means to generate 'response data (e.g. therapeutic effect on patient, degree of response to an agent, degree of induction, assay results or proliferation rate);

Correlating the extensive miRNA expression profile data set with response data for each cell population (e.g. using correlation methods as are known in the art);

Identifying correlating miRNA, preferably that correlate positively or negatively with a correlation coefficient of at least 7 or at least 8 (e.g. Pearson coefficient or other accepted correlation measure); and selecting such correlating miRNA as candidates for a miRNA expression panel for the cellular functional effect.

The invention further comprises a method of applying cells to a pre-determined purpose, the method comprising identifying, determining or inferring a cellular function effect of the cells for the predetermined purpose by the method defined above and in dependence of the identification, determination or inference applying the cells for the pre-determined purpose.

The invention according to this general embodiment further comprises a kit for use in inferring a cellular function effect of cells for use in a pre-determined purpose. The kit may comprise a miRNA or a panel of miRNAs (or equivalent reagents in a form suitable for an assay) and optionally a protocol and method for an assay and optionally a database or dataset relating to an indication of expression levels of miRNA associated with pre-defined and optionally validated expression levels. The kit may typically be for use in PCR (polymerase chain reaction), typically quantitative PCR and comprise primers for a miRNA or panel of miRNAs against which a cell population may be assayed.

The invention according to this embodiment further comprises a cell population selected or adapted to have a propensity or pre-determined degree of propensity for a cellular functional effect, preferably for a pre-determined purpose. Optionally, the degree of propensity may correspond to a correlation of at least plus or minus 0.8.

The cellular functional effect may be any suitable cellular functional effect which results in a functional outcome and is ideally applicable to a purpose, such as culture, bioprocess or therapy purposes. The cellular functional effect may be, for example, a propensity for a cell (e.g. a stem cell such as a mesenchymal stem/stromal cell) to differentiate to a particular cell lineage, e.g. when subject to an induction and/or disposed in a tissue type of that cell lineage. The cellular functional effect may be, for example, the migration potential or the engraftment potential of a cell (e.g. a stem cell) when administered in vivo. The cellular functional effect may be, for example, the propensity of a cell population to proliferate in culture and/or in vivo, optionally when induced. The cellular functional effect may be, for example, the propensity for the cells (e.g. mesenchymal stem cells) to secrete factors, such as paracrine factors when subject to an intervention such as particular culture conditions, an inducing agent or being disposed in tissue of a particular type. The cellular functional effect may, for example, the potential to be affected by particular factors and enzymes, for example the induction by interferon gamma of indoleamine-2,3-dioxygenase (IDO) in mesenchymal stem cells.

In accordance with the invention, a miRNA or panel of miRNAs may be used in uses or methods of the present invention applicable to a particular cell type or category or range of types of cell population.

In one embodiment, the cellular functional effect is the proliferation character or the propensity for a cell population to proliferate (or proliferation potential of a cell population). Such proliferation character may be proliferation when in in vitro culture, e.g. with inducement to proliferate. Preferably, the cells are assayed for miRNA expression against a miRNA or panel of miRNAs known to correlate with or be predictive of proliferation character or potential. Preferably, the cells or cell populations are mammalian cells, more preferably human cells. Preferably, the miRNA expression data is derived from a panel of miRNA, which preferably includes at least one miRNA positively correlated with proliferation and/or at least one miRNA negatively correlated with proliferation. Preferably, the panel of miRNA comprises at least two miRNA and more preferably up to six miRNAs, one or more and preferably all of which are selected from the aforementioned miRNAs. The cells or cell populations according to this embodiment may be any cell populations and preferably a mammalian cell populations, e.g. for use in bioprocess applications such as murine myeloma cells, Chinese hamster ovary cells, baby hamster kidney cells or human embryonic kidney cells, and more preferably human cell populations for various uses including in therapy, e.g. T-cells or stem cells.

In another embodiment, the cellular functional effect is the differentiation propensity or tendency to differentiate into one or more cell lineages. According to this embodiment, there is provided a miRNA or panel of miRNA for use according to the methods of the present invention, for example to assay one or more cell populations against for identifying, determining, inferring or predicting the likelihood or tendency of the cells to differentiate into a pre-determined or desired lineage tissue type (e.g. for further study, for application as a therapeutic etc). The panel may comprise candidates identified as defined above to indicate or infer a propensity or preference for the cells to differentiate into one or more of adipocytes, chondrocytes, osteocytes, myocytes, or one or more other lineages or sub-lineages common in various tissue types, such as skin, heart tissue, vascular tissue, fibrous extracellular tissue or nerve tissue. Preferably, the cells or cell populations are mammalian cells, more preferably human cells. In one preferred embodiment, a miRNA or panel of miRNAs are provided that are indicative of the propensity of cells or cell populations to differentiate into chondrocytes. Preferably, the miRNA expression data is derived from a panel of miRNA, which preferably includes at least one miRNA positively correlated with chondrogenesis and/or at least one miRNA negatively correlated with chondrogenesis. Preferably, the panel of miRNA comprises at least two miRNA and more preferably up to six miRNAs. In another preferred embodiment, a miRNA or panel of miRNAs are provided that are indicative of the propensity of cells or cell populations to differentiate into osteocytes. Preferably, the miRNA expression data is derived from a panel of miRNA, which preferably includes at least one miRNA positively correlated with osteogenesis and/or at least one miRNA negatively correlated with osteogenesis. Preferably, the panel of miRNA comprises at least two miRNA and more preferably up to six miRNAs.

Further, according to this embodiment, there is provided a kit for use to identify, determine or infer the propensity or relative propensity of cell populations for differentiation into a pre-defined or desired cell lineage such as adipocytes (adipogenesis), chondrocytes (chondrogenesis) and osteocytes (osteogenesis). A kit may typically be for use in quantitative PCR (polymerase chain reaction), for example, and comprise primers for a miRNA or panel of miRNAs known or identified as correlating with differentiation into the pre-defined or desired cell lineage, such as one of adipocytes (adipogenesis), chondrocytes (chondrogenesis) and osteocytes (osteogenesis). The kit may further comprise protocol and methods for the PCR assay. The kit may further comprise a set of miRNA samples from cell populations, which miRNAs are known or identified as correlating with differentiation into the pre-defined or desired cell lineage, such as one of adipocytes (adipogenesis), chondrocytes (chondrogenesis) and osteocytes (osteogenesis) and correspond with the miRNA primers and/or synthetic miRNA-specific oligonucleotides for the miRNA or panel of miRNAs. The kit may further comprise a database or indication of expression levels of miRNAs corresponding with a pre-defined validated extent of propensity to differentiate into the pre-defined or desired cell lineage such as one of adipocytes (adipogenesis), chondrocytes (chondrogenesis) and osteocytes (osteogenesis) and/or ranges of expression levels corresponding with different extents of differentiation into one of adipocytes (adipogenesis), chondrocytes (chondrogenesis) and osteocytes (osteogenesis) and/or recommended dosage levels (e.g. for regenerative cell therapy, e.g. in treating knee cartilage lesions) corresponding to determined miRNA expression levels.

In one embodiment, the pre-determined purpose is a bioprocess application. A bioprocess application may be a process for producing proteins (e.g. protein-based therapeutics such as monoclonal antibodies or enzymes). The invention may be used, for example, to select cell populations, cell batches or cell strains that may be productive for a particular purpose. The cells may be any cells for use in bioproduction systems such as those mentioned above for that purpose.

In one embodiment, the pre-determined purpose (or a further purpose) is therapy or diagnosis. The therapy may be stem cell therapy, such as regenerative therapy or immunomodulatory therapy. The therapy may be immuno-oncology therapy. The therapy may be heterologous, or homologous and may be allogenic or autologous.

In one embodiment, the pre-determined purpose is cell therapy, for example stem cell therapy, for example regenerative stem cell therapy. According to this embodiment, the invention further comprises a method of treatment of a human or animal patient in need thereof, the method comprising administering one or a plurality of therapeutic doses of cells to said patient, said cell therapy dose effective in treating said patient by a cellular function effect of the cells as between the cell therapy and the patient, the cellular function effect of the cells having been determined or inferred by use of miRNA expression profile, preferably by assaying the cells against miRNAs known or determined to be correlated with the cellular functional effect.

The cell therapy may optionally be for autologous, homologous or heterologous therapy, preferably homologous (e.g. autologous or allogenic).

Optionally, the pre-determined purpose may be donor, batch or cell population selection, for bioprocess or therapeutic purposes. Cells from different sources (e.g. different donors) or having different provenance (e.g. storage or culture conditions) may have variable propensity to demonstrate a cellular functional effect. For homologous (and heterologous) cell therapy, the invention finds particular application in the selection of donor cells or donor selection for cell therapy, especially for particular indication having specific requirements of the cells. Donor selection may be made according to any cellular functional effect for a pre-determined or further purpose, such as a property necessary for a bioprocess application or a therapeutic effect.

Optionally, the dose of cells to be administered may be determined. For autologous cell therapy in particular (but also for homologous and heterologous therapy), the invention finds application in the determination of dose of cells to be administered to a patient.

In one embodiment, the pre-determined purpose may be dose determination of a cell population for use in a therapy. The dose determination may be made based on the relative or actual propensity of the cells for a cellular functional effect which is associated with the efficacy or toxicity (or extent of side effect) of the cell population for the therapy. For actual rather than relative dose determination, it is preferred that the miRNA expression of pre-determined miRNAs is correlated to a determinable extent with a cellular functional effect associated with a therapeutic effect (efficacy thereof) which extent is validated and associated with one or more doses or ranges of doses.

The pre-determined purpose of the cells may be any further use, which typically depends upon a cellular functional effect for efficacy or for a desired level of efficiency. The pre-determined purpose may be, for example, for regenerative medicine or any type of cellular therapy on the human or animal body or cell culture or any other application, such as bioprocess or research applications for deriving new materials or the production of proteins or metabolites.

The cells may be any suitable cells for which there is an application associated with a cellular functional effect. The cells may be eukaryotic or prokaryotic (e.g. bacterial cells) but are preferably eukaryotic, more preferably mammalian cells.

Preferably the cells are human cells. Preferably the cells are stem cells or T-cells.

The cells, especially stem cells, may be sourced from one or multiple sources, which may be, for example, bone marrow, adipose tissue, peripheral blood, skeletal muscle, endometrium, placenta, umbilical cord blood, umbilical cord, Wharton's jelly, dental pulp and cells derived from pluripotent cells.

Further, according to this embodiment, the invention comprises cells for use in therapy by treatment or diagnosis, the cells selected or adapted to have a miRNA expression profile that have expression level (or patterns) commensurate or comparative with or having a degree of correlation with a pre-determined miRNA expression profile known or determined to be correlated with a cellular functional effect associated with said treatment or diagnosis.

Cell populations having a cellular functional effect identified, determined or inferred by the methods of this invention may be used for a variety of therapeutic applications and indications. Therapeutic applications include, for example: regenerative stem cell therapy, such as regeneration of target tissue such as cartilage, bone, adipose tissue, skin, muscle, heart tissue, vascular tissue, fibrous extracellular tissue, nerve tissue, etc by administration of stem cells pre-disposed or inducible to differentiate to lineages of such tissue or capable of inducing growth of such tissue by secretion of paracrine factors or by administration of in vitro induced differentiated tissue-specific cells derived from stem cells, which regenerative stem cell therapy may be useful in the treatment of tissue lesions, tissue degenerative conditions (such as in autoimmune disorders such as MS, Parkinson's disease or rheumatoid arthritis); regenerative stem cell transplantation such as bone marrow transplantation as part of a cancer therapy; immune-modulatory therapy using stem cells pre-disposed or induced with an immuno-modulatory effect for use in the treatment of immune disorders or responses, such as T-cell mediated immune disorders (e.g. Graft versus Host Disease), and such as rheumatoid arthritis, Crohn's disease and lupus; and targeted immuno-therapy such as immuno-oncology by the allogenic or autologous administration of T-cells pre-disposed or modified to target a tumour or target cancer cells, such as chimeric antigen receptor modified T-cells.

In one embodiment, the use and method is directed toward T-cells, autologous or allogenic, optionally modified, for use in therapy.

In one embodiment, the use and method is directed toward stem cells. The stem cells may be obtained from one or a mixed source of cells based upon expression of one or more cell surface markers.

In one embodiment, the use and method is directed toward mesenchymal stem cells for use in therapy.

In one embodiment, the use and method is directed toward haematopoietic stem cells. Such cells may be derived from bone marrow or peripheral blood. Such cells may comprise cells that are CD34+ cells.

A cell population for use in treating a patient may be characterized in that the cell population has a miRNA expression profile consistent with or correlating with a pre-determined expression profile for characterizing miRNAs for a particular purpose.

There are now described more particular embodiments of the invention falling within this general embodiment.

In one particular embodiment, the invention concerns the use of miRNA expression data of mesenchymal stem cells (MSCs) from donors or different donors (or categories of donors) to identify, determine or infer the propensity or relative propensity of those MSCs for indoleamine-2,3-dioxygenase (IDO) induction by interferon-gamma (IFN-γ). IDO induction is considered a surrogate for the immune-suppressive potential of MSCs, thus the present embodiment further provides the use of miRNA expression data of MSCs from donors or different donors (or categories of donors) to identify, determine or infer the propensity or relative propensity of those MSCs for immunosuppressive action on T cells (e.g. when administered to a patient, i.e. in vivo). Further, for indications involving inflammation or T-cell proliferation, such as Graft versus Host disease (e.g. in patients having received or receiving transplanted tissue from a donor, such as stem cell or bone marrow transplants), the invention according to this particular embodiment preferably provides use of miRNA expression data of mesenchymal stem cells (MSCs) from donors or different donors (or categories of donors) to identify, determine or infer the propensity or relative propensity of those MSCs for efficacy in anti-inflammatory activity, in indications implicating T-cell proliferation or in Graft versus Host disease. The same applies to batches of MSCs rather than MSCs from a donor or different donors.

Optionally, according to this particular embodiment, the miRNA expression profile may be validated against the cellular function or indication (e.g. Graft versus Host disease, e.g. in terms of inhibition of T-cell proliferation) whereby the miRNA expression profile levels may represent indicators of absolute efficacy (rather than relative efficacy) and thus, dose may be administered or selected accordingly.

Further, according to this particular embodiment, there is provided a method of identifying, determining or inferring propensity of MSCs from a donor or batch or different donors (or categories of donors) or batches for indoleamine-2,3-dioxygenase (IDO) induction by interferon-gamma (IFN-γ) (or for efficacy against or in the treatment of T-cell proliferation-mediated indications or in the treatment of Graft versus Host disease) the method comprising assaying cells against a pre-determined miRNA or panel of miRNAs known or determined to correlate with IDO induction by IFN-γ, generating miRNA expression data of the MSCs for the assayed miRNA or panel of miRNAs and identifying, determining or inferring therefrom the a propensity of the MSCs for the IDO induction by IFN-γ (or for efficacy against or in the treatment of T-cell proliferation-mediated indications or in the treatment of Graft versus Host disease). This may be achieved by comparing the expression data generated from the assay with expression levels (actual, e.g. ranges or thresholds, or relative), trends or patterns known to be associated (or correlated) with IDO induction of MSCs by IFN-γ (or for efficacy against or in the treatment of T-cell proliferation-mediated indications or in the treatment of Graft versus Host disease) and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with the IDO induction of MSCs by IFN-γ (or for efficacy against or in the treatment of T-cell proliferation-mediated indications or in the treatment of Graft versus Host disease). Preferably, a selection or decision may be made to provide an enhanced outcome or enhanced efficacy for the treatment of IDO induction-mediated therapy (e.g. in the treatment of T-cell proliferation-mediated indications or in the treatment of Graft versus Host disease) based on the identified, determined or inferred propensity (or relative propensity) of the MSCs for that cellular functional effect. That selection may be, for example, the selection of MSC populations that meet or exceed a pre-determined threshold of propensity for IDO induction by IFN-γ or the selection of donors (as individuals or determined donor groups determined or inferred to have a similar characteristic) for donation of MSCs for use in therapy (thus a method of donor selection is provided). That selection may be, for example, the selection of those MSC populations that better demonstrate propensity for IDO induction by IFN-γ (that is, have a better relative propensity) for use in therapy.

Optionally, the degree of correlation of the miRNA expression data may be validated against the functional outcome of the cellular functional effect in order to attribute an absolute value or a scale to the miRNA expression data or correlation thereof with the cellular functional effect or functional outcome from which a precise prediction or inference can be derived and thereby a decision or selection may optionally be made.

The invention according to this particular embodiment may further comprise a method of administering MSCs for therapy (in treatment of in the treatment of T-cell proliferation-mediated indications or in the treatment of Graft versus Host disease), the method comprising inferring (or determining) a propensity for IDO induction by IFN-γ in the MSCs by the method defined above and in dependence of the inference (or determination) applying the MSCs for the therapy.

The invention according to this particular embodiment further comprises a method for the treatment of the human or animal body by surgery, therapy or diagnosis by administering to a patient in need thereof MSCs selected to have a propensity for IDO induction. The invention according to this particular embodiment comprises MSCs for use in surgery, therapy or diagnosis, said MSCs selected to have a propensity for IDO induction.

Preferably the method and MSCs are for the treatment of conditions treatable by MSC-mediated T-cell suppression (or inflammatory or immune response disorders, typically involving T-cell proliferation), such as Graft versus Host Disease.

The propensity may be a relative propensity or an absolute propensity. Preferably, the MSCs having a propensity for IDO induction are MSCs that have a miRNA expression profile for a predetermined miRNA or panel of miRNAs known or identified to correlate with IDO induction (or efficacy in MSC-mediated T-cell suppression or in Graft versus Host disease), which said expression profile meets pre-determined expression criteria consistent with IDO induction potential. The pre-determined expression criteria may be, for example, that the expression profile correlates with miRNA expression in a standard or reference MSC that is known to be susceptible IFN-γ induction of IDO to a reasonable, definable extent, such correlation (e.g. Pearson correlation) being, for example, at least plus or minus 0.7 more preferably at least plus or minus 0.8, or that the expression levels of the miRNA or panel of miRNAs meets particular expression levels or ranges (e.g. that have been validated).

By expression data, it is meant expression levels, relative expression levels or expression profiles or patterns of miRNA of the cells.

Preferably, according to this particular embodiment, the miRNA expression data (or profile) is miRNA expression data from a miRNA or panel of miRNAs identified as having expression that correlates with IDO induction by IFN-γ. More preferably, the miRNA or panel of miRNAs have expression that correlates with IDO induction by IFN-γ with a correlation coefficient equal to or greater than 7.0, more preferably equal to or greater than 8.0.

Preferably, the miRNA or panel of miRNAs comprise (and more preferably consists) of miRNAs selected from one or more of hsa-miR-10b-5p, hsa-miR-136-5p, hsa-miR-140-3p, hsa-miR-23a-3p, hsa-miR-3651, hsa-miR-491-3p, hsa-miR-574-3p and hsa-miR-574-5p. Preferably, the miRNA expression data is derived from a panel of miRNA, which preferably includes at least one miRNA positively correlated with IDO induction by IFN-γ (e.g. hsa-miR-10b-5p) and/or at least one miRNA negatively correlated with IDO induction by IFN-γ (e.g. hsa-miR-136-5p, hsa-miR-140-3p, hsa-miR-23a-3p, hsa-miR-3651, hsa-miR-491-3p, hsa-miR-574-3p and hsa-miR-574-5p). Preferably, the panel of miRNA comprises at least two miRNA and more preferably up to six miRNAs.

Further, according to this particular embodiment, there is provided a kit for use to identify, determine or infer the propensity or relative propensity of MSCs from donors or different donors or categories of donors IDO induction by interferon-gamma (IFN-γ) or for other consequential or corresponding purpose. A kit may typically be for use in quantitative PCR (polymerase chain reaction), for example, and comprise primers for a miRNA or panel of miRNAs known or identified as correlating with IDO induction. The kit may further comprise protocol and methods for the PCR assay. The kit may further comprise a set of miRNA samples from MSCs, which miRNAs are known or identified as correlating with IDO induction and correspond with the miRNA primers and/or synthetic miRNA-specific oligonucleotides for the miRNA or panel of miRNAs. The kit may further comprise a database or indication of expression levels of miRNAs corresponding with a pre-defined validated extent of IDO induction and/or ranges of expression levels corresponding with different extents of IDO induction and/or recommended dosage levels (e.g. for cell therapy, e.g. in treating Graft versus Host disease) corresponding to determined miRNA expression levels. The miRNA or panel of miRNA are preferably as defined above.

Further, according to this particular embodiment, the miRNA or panel of miRNAs may further comprise (or consist) or may in the alternative comprise (or consist) of miRNAs selected from one or more of hsa-miR-106a-5p, hsa-miR-106b-5p, hsa-miR-129-5p, hsa-miR-137-3p, hsa-miR-145-5p, hsa-miR-151-5p, hsa-miR-17-5p, hsa-miR-181a-5p, hsa-miR-186-5p, hsa-miR-206-3p, hsa-miR-20a-5p, hsa-miR-214-3p, hsa-miR-300, hsa-miR-337-3p, hsa-miR-33a-5p, hsa-miR-33b-5p, hsa-miR-367-3p, hsa-miR-520d-5p, hsa-miR-539-5p, hsa-miR-543-3p, hsa-miR-580-3p, hsa-miR-675-3p, hsa-miR-720 and hsa-miR-93-5p (which are optionally considered a non-redundant set of predictive miRNAs). Preferably, the miRNA expression data is derived from a panel of miRNA, which preferably includes at least one non-redundant miRNA positively correlated with IDO induction by IFN-γ (or surrogate predictive marker thereof) and/or at least one non-redundant miRNA negatively correlated with IDO induction by IFN-γ (or surrogate predictive marker thereof). Preferably, the panel of miRNA comprises at least two miRNA and more preferably up to six miRNAs.

Alternatively, the cells may be instead of T cells, B cells, NK cells or DC cells, which offer a potential therapy autoimmune disorders (including GVHD, but also Multiple Scleroses or Crohn's disease).

In another particular embodiment, the invention concerns the use of miRNA expression data of mesenchymal stem cells (MSCs) from donors or different donors (or categories of donors) or from batches or different batches to identify, determine or infer the propensity or relative propensity of those MSCs for differentiation into adipocytes (adipogenesis), chondrocytes (chondrogenesis) or osteocytes (osteogenesis) and preferably to chondrocytes (chondrogenesis) or osteocytes (osteogenesis). The propensity to differentiate, e.g. into chondrocytes or osteocytes, has potential direct implications on clinical applications of MSCs in regenerative medicine, particularly in relation to the regeneration of tissue, such as bone, cartilage, muscle, ligament, tendon, and adipose tissues.

Further, for regenerative therapy indications, such as in the regeneration of tissue, such as bone cartilage, muscle, ligament, tendon and adipose tissue (e.g. in the regeneration of knee cartilage, such as in the treatment of articular cartilage lesions) the invention according to this particular embodiment preferably provides use of miRNA expression data of mesenchymal stem cells (MSCs) from donors or different donors (or categories of donors) to identify, determine or infer the propensity or relative propensity of those MSCs for efficacy in regenerative (and preventative) effect, in such indications requiring tissue regeneration. The same applies to batches of MSCs rather that MSCs from a donor or different donors.

Optionally, according to this particular embodiment, the miRNA expression profile may be validated against the cellular function or indication (e.g. knee cartilage repair, e.g. in terms of inhibition of propensity to differentiate into chondrocytes) whereby the miRNA expression profile levels may represent indicators of absolute efficacy (rather than relative efficacy) and thus, dose may be administered or selected accordingly.

Further, according to this particular embodiment, there is provided a method of inferring propensity of MSCs from a donor or batch or different donors (or categories of donors) or batches to identify, determine or infer the propensity or relative propensity of those MSCs for differentiation into adipocytes (adipogenesis), chondrocytes (chondrogenesis) and/or osteocytes (osteogenesis), e.g. for use in regenerative therapy, the method comprising assaying cells against a pre-determined miRNA or panel of miRNAs known or determined to correlate with propensity to differentiate into one of adipocytes (adipogenesis), chondrocytes (chondrogenesis) and/or osteocytes (osteogenesis), generating miRNA expression data of the MSCs for the assayed miRNA or panel of miRNAs and identifying, determining or inferring therefrom the propensity of the MSCs for differentiation into one of adipocytes (adipogenesis), chondrocytes (chondrogenesis) and/or osteocytes (osteogenesis) and thus propensity for efficacious regeneration of adipose tissue, cartilage tissue or bone. This may be achieved by comparing the expression data generated from the assay with expression levels (actual, e.g. ranges or thresholds, or relative), trends or patterns known to be associated (or correlated) with propensity of the MSCs for differentiation into adipocytes (adipogenesis), chondrocytes (chondrogenesis) and/or osteocytes (osteogenesis) and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with the propensity of the MSCs for differentiation into adipocytes (adipogenesis), chondrocytes (chondrogenesis) and/or osteocytes (osteogenesis). Preferably, a selection or decision may be made to provide an enhanced outcome or enhanced efficacy in regenerative therapy (according to the tissue type being regenerated) based on the identified, determined or inferred propensity (or relative propensity) of the MSCs for that cellular functional effect. That selection may be, for example, the selection of MSC populations that meet or exceed a pre-determined threshold of propensity for differentiation into one of adipocytes (adipogenesis), chondrocytes (chondrogenesis) or osteocytes (osteogenesis) or the selection of donors (as individuals or determined donor groups identified, determined or inferred to have a similar characteristic) for donation of MSCs for use in therapy (thus a method of donor selection is provided). That selection may be, for example, the selection of those MSC populations that better demonstrate propensity for differentiation into adipocytes (adipogenesis), chondrocytes (chondrogenesis) and/or osteocytes (osteogenesis) (that is, have a better relative propensity) for use in therapy.

Optionally, the degree of correlation of the miRNA expression data may be validated against the functional outcome of the cellular functional effect in order to attribute an absolute value or a scale to the miRNA expression data or correlation thereof with the cellular functional effect or functional outcome from which a precise prediction or inference can be derived and thereby a decision or selection may optionally be made.

The invention according to this particular embodiment may further comprise a method of administering MSCs for regenerative therapy (or selection for regenerative therapy, whether by direct administration or deriving or inducing progenitor or differentiated cells), the method comprising identifying, determining or inferring a propensity for differentiation into one of adipocytes (adipogenesis), chondrocytes (chondrogenesis) and/or osteocytes (osteogenesis) by the method defined above and in dependence of the identification, determination or inference applying the MSCs for the therapy (or using the MSCs to derive cells such induced differentiated cells or derived progenitor cells that may be used in therapy).

The invention according to this particular embodiment further comprises a method for the treatment of the human or animal body by surgery, therapy or diagnosis by administering to a patient in need thereof MSCs selected to have a propensity for differentiation into one of adipocytes (adipogenesis), chondrocytes (chondrogenesis) and osteocytes (osteogenesis), or differentiated cells derived therefrom. The invention according to this particular embodiment comprises MSCs (or differentiated cells derived from MSCs) for use in surgery, therapy or diagnosis, said MSCs selected to have a propensity for differentiation into one of adipocytes (adipogenesis), chondrocytes (chondrogenesis) and osteocytes (osteogenesis).

Preferably the method and MSCs are for the treatment of conditions treatable by regenerative cell therapy (especially regenerative stem cell therapy) such as MSC-mediated regenerative therapy, such as cartilage repair or regeneration, adipose tissue regeneration or bone repair or regeneration. For example, MSCs pre-disposed or having a greater propensity to differentiate into chondrocytes may provide enhanced efficacy in cartilage regenerative therapy, such as in the repair of cartilage lesions, whilst MSCs pre-disposed or having greater propensity to differentiate into osteocytes may provide enhanced efficacy in osteo-regenerative therapy, such as in the treatment of fractures or osteoporosis.

The propensity may be a relative propensity or an absolute propensity. Preferably, the MSCs having a propensity for differentiation into adipocytes (adipogenesis), chondrocytes (chondrogenesis) and/or osteocytes (osteogenesis) are MSCs that have a miRNA expression profile for a predetermined miRNA or panel of miRNAs known or identified to correlate with differentiation into adipocytes (adipogenesis), chondrocytes (chondrogenesis) and/or osteocytes (osteogenesis), which said expression profile meets pre-determined expression criteria consistent with differentiation into adipocytes (adipogenesis), chondrocytes (chondrogenesis)

and/or osteocytes (osteogenesis). The pre-determined expression criteria may be, for example, that the expression profile compares or correlates with miRNA expression in a standard or reference MSC that is known to have a propensity or relatively higher propensity for differentiation into adipocytes (adipogenesis), chondrocytes (chondrogenesis) and/or osteocytes (osteogenesis), e.g. to a reasonable, definable extent, such correlation (e.g. Pearson correlation) being, for example, at least plus or minus 0.7 more preferably at least plus or minus 0.8, or that the expression levels of the miRNA or panel of miRNAs meets particular expression levels or ranges (e.g. that have been validated).

By expression data, it is meant expression levels, relative expression levels or expression profiles or patterns of miRNA of the cells.

Preferably, according to this particular embodiment, the miRNA expression data (or profile) is miRNA expression data from a miRNA or panel of miRNAs identified as having expression that correlates with differentiation into respective one of adipocytes (adipogenesis), chondrocytes (chondrogenesis) and osteocytes (osteogenesis), more preferably that correlates with a correlation coefficient equal to or greater than plus or minus 7.0, more preferably equal to or greater than plus or minus 8.0.

Preferably, the miRNA expression data is derived from a panel of miRNA, which preferably includes at least one miRNA positively correlated with chondrogenesis and/or at least one miRNA negatively correlated with chondrogenesis. Preferably, the panel of miRNA comprises at least two miRNA and more preferably up to six miRNAs.

Preferably, the miRNA expression data and miRNA or panel of miRNAs for use in identifying, determining or inferring the propensity or relative propensity of MSCs to differentiate into osteocytes (osteogenesis) preferably includes at least one miRNA positively correlated with osteogenesis and/or at least one miRNA negatively correlated with osteogenesis. Preferably, the panel of miRNA comprises at least two miRNA and more preferably up to six miRNAs.

Further, according to this particular embodiment, there is provided a kit for use to identify, determine or infer the propensity or relative propensity of MSCs from donors or different donors or categories of donors for differentiation into one of adipocytes (adipogenesis), chondrocytes (chondrogenesis) and osteocytes (osteogenesis). A kit may typically be for use in quantitative PCR (polymerase chain reaction), for example, and comprise primers for a miRNA or panel of miRNAs known or identified as correlating with differentiation into one of adipocytes (adipogenesis), chondrocytes (chondrogenesis) and osteocytes (osteogenesis). The kit may further comprise protocol and methods for the PCR assay. The kit may further comprise a set of miRNA samples from MSCs, which miRNAs are known or identified as correlating with differentiation into one of adipocytes (adipogenesis), chondrocytes (chondrogenesis) and osteocytes (osteogenesis) and correspond with the miRNA primers and/or synthetic miRNA-specific oligonucleotides for the miRNA or panel of miRNAs. The kit may further comprise a database or indication of expression levels of miRNAs corresponding with a pre-defined validated extent of propensity to differentiate into one of adipocytes (adipogenesis), chondrocytes (chondrogenesis) and osteocytes (osteogenesis) and/or ranges of expression levels corresponding with different extents of differentiation into one of adipocytes (adipogenesis), chondrocytes (chondrogenesis) and osteocytes (osteogenesis) and/or recommended dosage levels (e.g. for regenerative cell therapy, e.g. in treating knee cartilage lesions) corresponding to determined miRNA expression levels. The miRNA or panel of miRNA are preferably as defined above for each purpose.

In another particular embodiment, the invention concerns the use of miRNA expression data of CD34+ cell populations to identify, determine or infer the propensity or relative propensity of those CD34+ cells to migrate toward Stromal cell-derived-factor 1 (SDF-1).

CD34+ cell populations are typically derived from blood or bone marrow and are used in autologous and allogenic therapy in a number of indications. To exert the desired therapeutic effect, appropriate dosing is necessary and this tends to be based upon cell count, an approach that has questionable legitimacy since the characteristics of the cells in any CD34+ cell population is variable and difficult to characterize. In particular, CD34+ cell populations can have highly variable numbers of haematopoietic stem and progenitor cells. Engraftment potential is considered to be related to the therapeutic efficacy of CD34+ cells and, associated therewith, SDF-1 migration potential is considered to correspond to the potential of such transplanted cells to migrate to specific tissues or sites of injury leading to engraftment.

It is believed that the in vivo SDF-1 migration potential of CD34+ cell populations is related to the therapeutic efficacy of CD34+. An SDF-1 migration assay has been used to show that SDF-1 migration potential corresponds with rate of engraftment after autologous cell transplantation (see:) and such an assay has been suggested as an alternative approach to assessing engraftment potential and dosing. However, the assay is convoluted and time consuming and incompatible with the time pressures of autologous CD34+ cell therapy.

This particular embodiment is directed toward a rapid screen that is a surrogate for an in vitro SDF-1 migration assay. The propensity or relative propensity of those CD34+ cells to migrate toward SDF-1 is determined from the propensity or relative propensity of those CD34+ cells to migrate toward SDF-1 according to an in vitro SDF-1 migration assay. The use is directed toward the engraftment of stem cells in autologous stem cell therapy.

Indications for autologous or allogenic CD34+ haematopoietic stem cell therapy include haematopoietic reconstitution in the treatment of cancers (such as leukaemias), metastatic breast cancer, neuroblastoma, cardiovascular diseases such as myocardial ischemia (e.g. to increase exercise capacity), myocardial infarction and ischemic stroke, multiple sclerosis and autoimmune disorders. The application of this particular embodiment has particular utility in autologous therapy.

The use according to this particular embodiment is preferably directed toward determining or inferring graft potential of CD34+ cell populations and thus would be useful in determining a dose for autologous CD34+ haematopoietic stem cell therapy.

Optionally, according to this particular embodiment, the miRNA expression profile may be validated against the SDF-1 migration assay whereby the miRNA expression profile levels may represent indicators of absolute graft potential and thus a dose may be administered or selected accordingly.

Further, according to this particular embodiment, there is provided a method of identifying, determining or inferring propensity of CD34+ cell populations for SDF-1 migration potential for use in CD34+ stem cell therapy, especially autologous therapy, the method comprising assaying cells against a pre-determined miRNA or panel of miRNAs known or determined to correlate with SDF-1 migration potential (typically by way of correlating with SDF-1 migration in an in vitro assay), generating miRNA expression data of the CD34+ cell population for the assayed miRNA or panel of miRNAs and identifying, determining or inferring therefrom the propensity of the of CD34+ cell populations for SDF-1 migration potential (or engraftment potential) for use in CD34+ stem cell therapy. This may be achieved by comparing the expression data generated from the assay with expression levels (actual, e.g. ranges or thresholds, or relative), trends or patterns known to be associated (or correlated) with propensity of the of CD34+ cell populations for SDF-1 migration potential and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with the propensity of the of CD34+ cell populations for SDF-1 migration potential.

Preferably, a determination as to the dose of CD34+ cells to be used in therapy may be made to enhance efficacy of the CD34+ stem cell therapy based on the determined propensity of the CD34+ cells for that cellular functional effect. That determination as to dose may be based upon, for example, comparison (e.g. expression levels or patterns) or correlation of the miRNA expression data for a population of the CD34+ cells to be administered with levels or pattern of expression of the miRNA or panel of miRNAs known to correlate with and validated against the cellular functional effect (that is, SDF-1 migration potential as determined by in vitro assay), or even functional outcome in vivo. Thus, one may attribute an absolute value or a scale to the miRNA expression data or correlation thereof with the cellular functional effect or functional outcome from which a precise prediction or inference can be derived and thereby a determination as to dose may be made.

The invention according to this particular embodiment may further comprise a method of administering CD34+ cell populations for therapy (in autologous stem cell therapy, for example), the method comprising identifying, determining or inferring a propensity for SDF-1 migration potential of the CD34+ cell population by the method defined above and in dependence of the identification, determination or inference applying the CD34+ cells for the therapy.

The invention according to this particular embodiment further comprises a method for the treatment of the human or animal body by surgery, therapy or diagnosis by administering to a patient in need thereof a CD34+ cell dose selected to have a propensity for SDF-1 migration. The invention according to this particular embodiment comprises CD34+ cells for use in surgery, therapy or diagnosis, said CD34+ cell populations selected to have a propensity for SDF-1 migration.

Preferably the method and CD34+ cell populations are for the treatment of conditions treatable by CD34+ haematopoietic stem cell-mediated therapy, such as one or more of those indications mentioned above in connection with this particular embodiment.

The propensity may be a relative propensity or an absolute propensity. Preferably, the CD34+ cell populations having a propensity for SDF-1 migration are CD34+ cell populations that have a miRNA expression profile for a predetermined miRNA or panel of miRNAs known or identified to correlate with SDF-1 migration, which said expression profile meets pre-determined expression criteria consistent with SDF-1 migration potential. The pre-determined expression criteria may be, for example, that the expression profile correlates with miRNA expression in a standard or reference CD34+ cell population that is known to have a high propensity (or defined or desirable propensity) for SDF-1 migration to a reasonable, definable extent, such correlation (e.g. Pearson correlation) being, for example, at least plus or minus 0.7 more preferably at least plus or minus 0.8, or that the expression levels of the miRNA or panel of miRNAs meets particular expression levels or ranges (e.g. that have been validated).

By expression data, it is meant expression levels, relative expression levels or expression profiles or patterns of miRNA of the cells.

Preferably, according to this particular embodiment, the miRNA expression data (or profile) is miRNA expression data from a miRNA or panel of miRNAs identified as having expression that correlates with SDF-1 migration potential. More preferably, the miRNA or panel of miRNAs have expression that correlates with SDF-1 migration potential with a correlation coefficient equal to or greater than 7.0, more preferably equal to or greater than 8.0.

Preferably, the miRNA or panel of miRNAs comprise (and more preferably consists) of miRNAs selected from one or both of has-miR-1471 and has-miR-1288-3p. Both these miRNAs have a positive correlation with SDF-1 migration potential.

Further, according to this particular embodiment, there is provided a kit for use to identify, determine or infer the propensity or relative propensity of CD34+ cell populations to SDF-1 migration potential or for other consequential or corresponding purpose. A kit may typically be for use in quantitative PCR (polymerase chain reaction), for example, and comprise primers for a miRNA or panel of miRNAs known or identified as correlating with SDF-1 migration potential. The kit may further comprise protocol and methods for the PCR assay. The kit may further comprise a set of miRNA samples from CD34+ cell populations, which miRNAs are known or identified as correlating with SDF-1 migration potential and correspond with the miRNA primers and/or synthetic miRNA-specific oligonucleotides for the miRNA or panel of miRNAs. The kit may further comprise a database or indication of expression levels of miRNAs corresponding with a pre-defined validated extent of SDF-1 migration and/or ranges of expression levels corresponding with different extents of SDF-1 migration and/or recommended dosage levels (e.g. for cell therapy) corresponding to determined miRNA expression levels. The miRNA or panel of miRNA are preferably as defined above.

In another particular embodiment, the invention concerns the use of miRNA expression data of T-cells from a donor (or modified T-cells) to identify, determine or infer the propensity or relative propensity of those T-cells for proliferation.

Immunotherapies based upon cell-based adoptive transfer of T-cells are showing great promise and very effective results in treatment of certain conditions, notably oncology indications. Typically, autologous therapies involve donor T-cells from a patient that are optionally subject to a modification (e.g. to surface antigens to target a tumour) and are tumour reactive. Allogenic therapies are also under development and in clinical trials. These donor T-cells or modified donor T-cells are expanded in vitro before administration to a patient in therapy. A critical constraint and technical challenge for such therapy is the ability to generate therapeutically suitable numbers of cells. It would be advantageous at an early stage of a process to be able to screen a donor or a donor's T-cells for proliferation potential or proliferation rate in the development of a therapy. This particular embodiment provides a screen for proliferation potential of donor T-cells which may be used in immunotherapies, especially immuno oncology therapies, such as cell-based adoptive transfer of T-cells.

T-cell populations (or modified T-cell populations) for use in such therapeutic applications require to be expanded to provide therapeutic doses for patients.

Indications for autologous or allogenic T-cell based immunotherapies, such as by cell-based adoptive transfer of T-cells, include autoimmune disorders and cancers such as solid tumors, cervical cancer, lymphoma, leukamias, bile duct cancer, neuroblastoma, lung cancer, breast cancer, sarcoma, melanoma, CD19-expressing haematologic malignancies and CD19+ B cell malignancies, including B-cell acute lymphoblastic leukaemia (which may harbor rearrangement of the mixed lineage leukaemia), and may be mediated by, for example, chimeric antigen receptor modified T-cells.

The use according to this particular embodiment is preferably directed toward identifying, determining or inferring proliferation potential of T-cell or modified T-cell populations and thus would be useful in determining the suitability of a donor for development of a T-cell based therapeutic or in determining the quantity of donor T-cell material required to expand to a therapeutic dose in a pre-determined time.

Optionally, according to this particular embodiment, the miRNA expression profile may be validated against proliferation rate whereby the miRNA expression profile levels may represent indicators of absolute proliferation potential and thus a decision or selection may be made accordingly.

Further, according to this particular embodiment, there is provided a method of identifying, determining or inferring propensity of T-cell or modified T-cell populations for proliferation potential for use in cell-based adoptive transfer T-cell therapy, especially autologous therapy, the method comprising assaying cells against a pre-determined miRNA or panel of miRNAs known or determined to correlate with T-cell proliferation potential, generating miRNA expression data of the T-cell population for the assayed miRNA or panel of miRNAs and identifying, determining or inferring therefrom the a propensity of the T-cell population for proliferation potential. This may be achieved by comparing the expression data generated from the assay with expression levels (actual, e.g. ranges or thresholds, or relative), trends or patterns known to be associated (or correlated) with proliferation and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with proliferation potential or rates. Preferably, a determination as to the quantity of T-cells required from the donor, or the suitability of the donor for developing a therapy, may be made. That determination may be based upon, for example, a comparison (or degree of correlation) of the miRNA expression data for the miRNA or panel of miRNA the expression levels or patterns of which are validated against the cellular functional effect (that is, proliferation potential), in order to attribute an absolute value or a scale to the miRNA expression data or correlation thereof with the cellular functional effect or functional outcome from which a precise prediction or inference can be derived and thereby a determination as to dose may be made.

The invention according to this particular embodiment may further comprise a method of administering T-cell or modified T-cell populations for therapy (in autologous or allogenic cell-based adoptive transfer T-cell therapy, for example), the method comprising inferring (or determining) a propensity for proliferation potential of the donor T-cell or modified T-cell population by the method defined above and in dependence of the inference (or determination), modifying and expanding the T-cells to a therapeutic dose and applying the T-cell dose for the therapy.

The invention according to this particular embodiment further comprises a method for the treatment of the human or animal body by surgery, therapy or diagnosis by administering to a patient in need thereof a T-cell or modified T-cell dose selected to have a propensity for proliferation. The invention according to this particular embodiment comprises T-cell populations or modified T-cell populations for use in surgery, therapy or diagnosis, said T-cell populations selected to have a high propensity for proliferation.

Preferably the method and T-cell populations are for the treatment of conditions treatable by cell-based adoptive transfer of T-cells, such as by CAR T-cell therapy.

The propensity may be a relative propensity or an absolute propensity. Preferably, the T-cell populations having a propensity for proliferation are T-cell populations that have a miRNA expression profile for a predetermined miRNA or panel of miRNAs known or identified to correlate with a high proliferation potential, which said expression profile meets pre-determined expression criteria consistent with high proliferation potential. The pre-determined expression criteria may be, for example, that the expression profile compares or correlates with miRNA expression in a standard or reference T-cell population that is known to have a high propensity (or defined or desirable propensity) for proliferation to a reasonable, definable extent, such correlation (e.g. Pearson correlation) being, for example, at least plus or minus 0.7 more preferably at least plus or minus 0.8, or that the expression levels of the miRNA or panel of miRNAs meets particular expression levels or ranges (e.g. that have been validated).

By expression data, it is meant expression levels, relative expression levels or expression profiles or patterns of miRNA of the cells.

Preferably, according to this particular embodiment, the miRNA expression data (or profile) is miRNA expression data from a miRNA or panel of miRNAs identified as having expression that correlates with high proliferation potential. More preferably, the miRNA or panel of miRNAs have expression that correlates with high proliferation potential with a correlation coefficient equal to or greater than 7.0, more preferably equal to or greater than 8.0.

Preferably, the miRNA expression data is derived from a panel of miRNA, which preferably includes at least one miRNA positively correlated with proliferation and/or at least one miRNA negatively correlated with proliferation. Preferably, the panel of miRNA comprises at least two miRNA and more preferably up to six miRNAs.

Further, according to this particular embodiment, there is provided a kit for use to identify, determine or infer the propensity or relative propensity of T-cell populations to proliferation potential or for other consequential or corresponding purpose. A kit may typically be for use in quantitative PCR (polymerase chain reaction), for example, and comprise primers for a miRNA or panel of miRNAs known or identified as correlating with high (or desirable) proliferation potential. The kit may further comprise protocol and methods for the PCR assay. The kit may further comprise a set of miRNA samples from T-cell populations, which miRNAs are known or identified as correlating with a proliferation potential and correspond with the miRNA primers and/or synthetic miRNA-specific oligonucleotides for the miRNA or panel of miRNAs. The kit may further comprise a database or indication of expression levels of miRNAs corresponding with a pre-defined validated extent of proliferation and/or ranges of expression levels corresponding with different extents of proliferation recommended donor quantities for expansion corresponding to determined miRNA expression levels. The miRNA or panel of miRNA are preferably as defined above.

Whilst the invention defined herein refers to identifying, determining or inferring a propensity for a cellular functional effect, it may likewise be defined as identifying, determining or inferring whether or not there will be (or is likely to be) a cellular functional effect or a sufficient or desirable level of a cellular functional effect. In this general embodiment, this directed in particular toward a cell or cell population, it may be used to predict functional outcomes and make determinations and selection or take action determined therefrom.

In a second general embodiment, it concerns use of miRNA expression data derived from target tissue or target cells (e.g. a prospective patient) to which a cell population is to be applied (e.g. for treatment by a pre-determined cell therapy) to determine the propensity for that cell population (e.g. cell therapy) to have a particular effect on the target tissue or target cells (in the prospective patient).

Target tissue is intended to include various tissue types within which cells relevant to, for example, a therapeutic treatment may exist or move to. Target tissue includes biofluids, such as blood plasma. Target tissue includes tissue to which treatment effects are to be applied, but include other tissues where indications or predictions of treatment by miRNA expression profiles may be determinable.

Thus, the miRNA expression data can be used to stratify a patient population for receiving the cell therapy.

The use preferably is by assaying cells or tissue from a patient (or multiple patient) against a pre-determined miRNA or panel of miRNA, the expression of which is already identified as associated or correlated with the cellular functional effect of a cell or a known surrogate or assay or other process associated with the cellular functional effect. The panel of miRNA may comprise any number of miRNA, the expression of which are typically correlated with the cellular functional effect (or another assay or process considered equivalent to the cellular functional effect) and may be positively or negatively correlated or may comprise one or more miRNA positively correlated with the cellular functional effect and/or one or more miRNA negatively correlated with the cellular functional effect. Preferably, the panel of miRNA comprises at least two miRNA and preferably up to six miRNA.

By expression data, it is meant expression levels, relative expression levels or expression profiles or patterns of miRNA of the cells.

The miRNA expression data is preferably expression data for a miRNA or panel of miRNAs of the cells, the miRNA or panel of miRNAs known or determined as having expression, expression levels or an expression profile correlating with the cellular functional effect (or known surrogate or assay or marker for or associated with the cellular functional effect).

Preferably, the miRNA expression data is expression data for two to six miRNAs having a pre-determined correlating effect with the cellular functional effect and preferably wherein at least one miRNA is positively correlated and at least one miRNA is negatively correlated with the cellular functional effect.

The cellular functional effect according to this general embodiment is a functional effect of a cell to be used for a further or pre-determined use which cellular functional effect is typically not readily demonstrable in the cells until after the cell has been put to that further or pre-determined use or by some other assay of the cells. Preferably, cellular functional effect can be said to be a characteristic of the manner in which cells interact at a cellular level in vivo or in vitro (according to the pre-determined purpose).

A cellular functional effect is preferably a functional effect of a cell or cell population or functional outcome of application of the cell or cell population for a purpose, which effect is separated temporally, procedurally or interventionally from the cells or cell population from which the inference or identification is being made (by means of assaying for miRNA expression).

Preferably, the cellular functional effect, the propensity for which a population of cells is identified, determined or inferred as having according to an aspect of the present invention, in dependence upon non-coding or miRNA expression data or an expression profile (the predictive data or predictive profile) derived from the population of cells, is not contemporaneous with the predictive data or predictive profile. Preferably, the cellular functional effect is separated in time from the predictive data or predictive profile, by which it is meant from time at which the predictive data or predictive profile is derived from a population of cells or sample thereof. The separation in time may be any suitable time such as at least 15 minutes, at least an hour, at least 24 hours, at least 1 week or at least 1 month. This non-contemporaneous nature may be better defined in terms of cell passages, e.g. separated by at least one passage, at least two passages, at least 6 passages or at least 12 passages.

Optionally, according to an embodiment of the present invention, the cellular functional effect is not demonstrable in the cell population from which the non-coding RNA or miRNA expression data or profile derives (at the time a sample is taken for deriving such expression data or profile), but only after a passage of time, application of a process or procedure, or of an intervention on the cell population.

In a preferred embodiment of the use and method of the invention, non-coding RNA or miRNA expression data or expression profile may be derived from a population of cells (e.g. a first population of cells) at a first occasion for use in identifying, determining or inferring the propensity for a cellular functional effect in a population of cells (e.g. a second population of cells) at a second occasion. The second occasion and first occasion are typically separated temporally, by process or by intervention on the cell population. The second population of cells preferably derives from the first population of cells by the passage of time, application of a process or an intervention on the first population of cell.

It is a preferred embodiment of the invention that the use and method is for predicting a cellular functional effect (and optionally a functional outcome) in a population of cells that is to be subject to a passage of time, application of a process or procedure or subject to an intervention and in particular to predict the cellular functional effect (or identify, determine or infer the propensity thereof) in a population of cells after a passage of time, application of a process or procedure or after an intervention, based upon non-coding RNA or miRNA expression data or expression profiles derived from the population of cells before the passage of time, the application of the process or procedure or before the intervention.

The use according to this embodiment is preferably intended to enable prediction, determination or inference as to propensity of a cellular functional effect to occur in a target tissue in response to treatment by a population of cells leading to a functional outcome for use in a pre-determined purpose. The target tissue is preferably tissue of or derived from a patient or prospective patient and the treating population of cells is preferably a therapeutic population of cells for cell therapy. The cellular functional affect according to this general embodiment is preferably a cellular functional effect as between the target tissue and the treating population of cells and may be an effect on the target tissue by the cells or an effect by the treating population of cells in the environment of the target tissue. Preferably, this is in order to make a selection as to target tissue or patients capable of benefiting from administration of the treating population of cells or cell therapy or in order to make a determination as to dose of the cell therapy for a particular patient (e.g. where the extent of the cellular functional effect is variable and determinable).

A pre-determined purpose according to this general embodiment is a purpose or use of the cells that the cellular functional effect has or is associated with. The pre-determined purpose may be any purpose to which cells can be put which rely on some functional effect of the cells (and a functional outcome of applying the cells). The pre-determined purpose may be, typically, a cell therapy application.

A cell therapy application according to this general embodiment may be, for example, a cancer therapy (such as a treatment of a cancer with an immune-oncology therapy by administering therapy with T-cells pre-disposed or modified to target a tumour or cancer cells, such as chimeric antigen receptor modified T-cells), regenerative stem cell transplantation (e.g. bone marrow transplant), regenerative stem cell therapy or treatment of autoimmune disorders, such as Crohn's disease or Multiple Scleroses or T-cell mediated immune disorders (e.g. with stem cells, for example, stem cells pre-disposed or induced with an immune-modulatory effect) or any other treatment mentioned hereinbefore.

The invention according to this general embodiment further comprises a method of inferring propensity of a cellular functional effect for a pre-determined purpose as between a treating population of cells (e.g. a cell therapy) and a target tissue (e.g. of a patient), the method comprising assaying cells of the target tissue against a pre-determined miRNA or panel of miRNAs known or determined to correlate with a desired or intended cellular functional effect (or extent thereof) of the treating population of cells on or in the presence of a target tissue, generating miRNA expression data of the cells for the assayed miRNA or panel of miRNAs and therefrom identifying, determining or inferring the propensity for treating the population of cells for the cellular functional effect on or in relation to that target tissue (or patient or patient sub-group). This may be achieved by comparing the expression data generated from the assay with expression levels (actual, e.g. ranges or thresholds, or relative), trends or patterns known to be associated (or correlated) with the propensity for treating the population of cells for the cellular functional effect on or in relation to that target tissue (or patient or patient sub-group) and optionally determining from the degree of similarity or correlation with trends or patterns inferring a relative or actual propensity. For a panel of miRNAs, the expression data generated may be compared with a pattern for the panel and a determination made according to a degree of correlation with a pattern associated with or correlated with the propensity for treating the population of cells for the cellular functional effect on or in relation to that target tissue (or patient or patient sub-group). Preferably, a selection or decision may be made to provide an enhanced functional outcome or enhanced efficacy of the pre-determined purpose based on the determined propensity (or relative propensity) for the cellular functional effect. That selection may be, for example, the selection or stratification of patients suitable for receiving the cell therapy or determination of dose of cell therapy for a patient or category of patient.

Optionally, the degree of correlation of the miRNA expression data may be validated against the functional outcome of the cellular functional effect in order to attribute an absolute value or a scale to the miRNA expression data or correlation thereof with the cellular functional effect or functional outcome from which a precise prediction or inference can be derived and thereby a decision or selection may optionally be made.

The invention further comprises a method of applying a treating population of cells to a pre-determined purpose in relation to a target tissue (e.g. of a patient), the method comprising inferring (or determining) a cellular function effect as between the treating cells and the target tissue for the predetermined purpose by the method defined above and in dependence of the inference (or determination) applying the cells for the pre-determined purpose.

The invention according to this general embodiment further comprises a method of identifying or determining one or more miRNA the expression of which in a target tissue or cells of or indicative of the target tissue (e.g. in a prospective patient) being assayed is correlating with a cellular functional effect of the cell population to be administered to or for treating the target tissue (e.g. administered to a patient), preferably for a predetermined purpose such as cell therapy, for use of said one or more miRNAs in a panel for identifying, determining or inferring the propensity of the cellular functional effect in relation to the target tissue. The method preferably comprises:

identifying target tissue (or cells from or indicative of target tissue) from multiple target tissue sources (e.g. different prospective patients—ideally patients from different patient groups or patients known or expected to show variable effects) and optionally sourcing or sampling said target tissue;

Treating and using a first target tissue sample of each target tissue to isolate total RNA for miRNA expression profiling (e.g. using Agilent miRNA microarrays: one version of which, Agilent MiRBase version 16, contains 1199 human miRNAs; and another version of which, Agilent MiRBase version 21, contains 2549 human miRNAs) thereby generating an extensive (e.g. based on at least 100 miRNAs, preferably at least 800, more preferably at least 1000 and most preferably at least 2000 miRNAs) miRNA expression profile data set for each target tissue;

Subjecting each target tissue (e.g. a sample of the target tissue in vitro or the target tissue in vivo the latter being subjecting target tissue in each prospective patient) to a treatment by a treating cell population designed to elicit a cellular functional effect of the treating cell population in the target tissue (said treating being, for example, administration to a patient with a target indication a dose of the treating cell population) and the extent of the cellular functional effect monitored by a known or conventional or surrogate means to generate 'response data (e.g. therapeutic effect on patient or patient target tissue);

Correlating the extensive miRNA expression profile data set with response data to the treating cell population by each target tissue (e.g. using correlation methods as are known in the art);

Identifying correlating miRNA, preferably that correlate positively or negatively with a correlation coefficient of at least 7 or at least 8 (e.g. Pearson coefficient or other accepted correlation measure); and selecting such correlating miRNA as candidates for a miRNA expression panel for the cellular functional effect.

The invention according to this general embodiment further comprises a kit for use in identifying, determining inferring a cellular functional effect as between a treating population of cells (e.g. for cell therapy) and a target tissue (e.g. of a prospective patient), the kit comprising primers for use in quantitative PCR (polymerase chain reaction), primers being for a miRNA or panel of miRNAs known or identified as correlating with the cellular functional effect, optionally as further described above. Optionally, the kit further comprises a protocol and methods for the PCR assay.

The invention according to this general embodiment further provides a companion diagnostic for a cell therapy, the companion diagnostic comprising a kit, particular to the cell therapy, as defined above.

The invention according to this general embodiment further provides a cell therapy system comprising a cell therapy and a corresponding companion diagnostic as defined above.

The present general embodiment further provides use of miRNA expression data derived from a patient in need of treatment for a disease to stratify that patient as sufficiently responsive or not sufficiently responsive to a pre-defined cell therapy for treatment of the disease. In this case the cellular function could be said to be the efficacy of the cell therapy in the particular patient. There is thus further provided use of miRNA expression profiles to stratify patients according to a particular cell therapy.

References herein to miRNAs and to particular miRNAs use miRNA ID codes (miRNA identifiers) following the convention on naming described on www.mirbase.org, a registry and database of miRNAs managed by the Griffiths-Jones lab from the University of Manchester with funding from the BBSRC. The miRNA identifiers are those valid at 2 May 2016.

EXAMPLES

Examples are given from different cell types and a variety of functional outcomes to further illustrate that miRNA expression can be used to predict downstream functional outcomes and therefore could be used donor screening, dose determination and cell therapy.

Example 1—IDO Induction Potential of MSCs

The induction of indoleamine-2,3-dioxygenase (IDO) has been shown to correlate with reduced T-cell proliferation and be responsible for the immunosuppressive action of mesenchymal stem cells (MSCs) on T-cells. MSCs from different donors (and potentially different categories of donors) are known to induce IDO to varying degrees and so the immunosuppressive action of MSCs on T-cells can vary from donor to donor.

It was postulated by the inventors that miRNA profile data may be used to predict or infer IDO induction by MSCs from a particular donor by screening the donor's cells prior to extensive cell expansion.

To identify a panel of miRNA which can form the basis of a rapid screen for IDO potential, human bone-marrow-derived MSCs from seven independent donors were sourced from RoosterBio, Inc. The donor information is summarized in Table 1 below:

TABLE 1

| Donor | Age (years) | Gender | PDL* | Cell lot number |
|---|---|---|---|---|
| 1 | 22 | Male | 8.69 | 00056 |
| 2 | 43 | Male | 7.32 | 00009 |
| 3 | 33 | Male | 7.91 | 00012 |
| 4 | 29 | Female | 7.37 | 00016 |
| 5 | 20 | Female | 8.86 | 00071 |
| 6 | 23 | Male | 8.45 | 00048 |
| 7 | 25 | Male | 8.16 | 0082 |

*Population doubling levels post mononuclear cell isolation

Frozen vials of human bone-marrow-derived MSCs from the seven independent donors (each containing $1\times10^7$ cells) were thawed out and re-suspended in 37° C. RoosterBio™ High Performance media (cat. no KT-001) to give a cell suspension of $1\times10^6$ cells per mL. An aliquot from each donor of $2\times10^6$ cells was generated and immediately centrifuged at 300×g for 5 minutes at room temperature. The remaining cells from the vial were used for seeding tissue culture flasks for cell expansion (see below). After centrifugation of the $2\times10^6$ cell aliquots, the supernatant was removed by pipette and the cells re-suspended in 5 mL of ice-cold phosphate buffer saline pH 7.0 (PBS) and centrifuged at 300×g for 5 minutes at 4° C. This step was repeated and the cells re-suspended in 1 mL of ice-cold PBS, transferred to a 1.5 mL microfuge tube. This was centrifuged at 300×g for 5 minutes at 4° C. and the supernatant removed by pipette. The resulting cell pellet was further centrifuged 300×g for 1 min at 4° C. to collect any residual PBS. This was removed by pipette and the cell pellet snap-frozen in liquid nitrogen and stored at −80° C. until used for RNA isolation within two weeks of generation.

All MSC culture was carried out at 37° C. in 95% standard sea level air: 5% carbon dioxide atmosphere. Human bone-marrow-derived MSCs from the 7 independent donors were each seeded in 1×T225 tissue culture flasks at 5000 viable cells per $cm^2$ and expanded in fully supplemented RoosterBio™ High Performance Media for 3-4 days (80-90% confluence) with no media change. After expansion in T225 tissue culture flasks, the cells were harvested by trysinisation using TrypLE™ Express 1 x enzyme (Thermo Fisher Scientific cat no. 12605036). For the IDO-induction assay, cells were seeded at confluence at 40,000 cells per $cm^2$ in 60 mm or 6-well plates (BD Falcon) in 4.4 or 2 mL RoosterBio™ High Performance media. After 24 h, media was changed to RoosterBio™ basal media (cat. no. SU-005) supplemented with 2% Foetal Bovine Serum. After 1 h, cells to be induced were treated with 10 ng per mL IFN-γ (Thermo Fisher Scientific cat no. RIFNG50), whilst control cells received no treatment. After 24 h±1 h, cell culture supernatant was collected and frozen at 80° C. until assayed for IDO-induction and activity.

IDO induction and activity was assayed by quantifying kynurenine secreted into the cell culture supernatant. N-formylkynurenine was hydrolysed to kynurenine by 30% (w/v) trichloroacetic acid. These were then treated with 1% w/v p-dimethylaminobenzaldehyde in acetic acid, which interacts with kynurenine to give a yellow product. Kynurenine levels were assessed by measuring the absorbance in the processed cell culture supernatants at 480 nM in a spectrophotometer and then comparing the resulting absorbance units to a 0-10 μg per ml L-kynurenine standard curve (Sigma-Aldrich cat. no K8625). IDO-induction was calculated by normalising kynurenine levels to the number of cells in the well and days of incubation and expressed as pg kynurenine secreted per cell per day. Levels of IDO-induction are given in Table 2 below:

TABLE 2

| Donor | Control no IFN-γ | Plus IFN-γ |
|---|---|---|
| 1 | 0.00 | 52.2* |
| 2 | 0.20 | 67.6 |
| 3 | 0.00 | 43.6 |
| 4 | 0.20 | 26.5 |
| 5 | 0.00 | 14.5 |
| 6 | 0.11 | 11.8 |
| 7 | 0.00 | 46.0 |

*IDO-induction, pg kynurenine secreted per cell per day

Total RNA (containing all RNA species, including small non-coding RNAs such as miRNAs) was isolated from the cell pellets from cryopreserved cells using the Exiqon miR-CURY™ RNA Isolation Kit-Cell & Plant (cat. no. 300110) according to the manufacturer's instructions v2.2. Total RNA concentrations were measured using a Nanodrop™ 1000 spectrophotometer. RNA purity and quality were assessed as 'pure' based on 260/280 nM and 260/230 nM ratios and 'high' RNA Integrity Numbers (RINs) generated using an Agilent TapeStation 2200—these are summarized in Table 3 below:

TABLE 3

| Donor | 260/280 nM ratio[A] | 260/230 nM ratio[B] | RIN[C] |
|---|---|---|---|
| 1 | 2.03 | 2.17 | 10.0 |
| 2 | 2.09 | 2.16 | 9.0 |
| 3 | 2.08 | 2.24 | 10.0 |
| 4 | 2.06 | 2.18 | 10.0 |
| 5 | 2.06 | 2.15 | 10.0 |
| 6 | 2.07 | 2.00 | 10.0 |
| 7 | 2.07 | 2.00 | 10.0 |

[A]260/280 ratio assesses protein contamination and RNA with a ratio of ~2.0 is considered 'pure'
[B]260/230 ratio assesses organic chemical contamination and RNA with a ratio of 2.0-2.2 is considered 'pure'
[C]RINs assess RNA quality/degradation. RNA with a RIN of ≥7.0 is considered good quality, undegraded RNA, RNA with the maximum RIN of 10 being the highest quality For miRNA expression analysis using microarrays, aliquots of each donor sample RNA were diluted to 50 ng per mL using nuclease-free water and stored at 80° C. until analysed. Samples were analysed on the Agilent Technologies, Inc. miRNA microarray platform (SurePrint G3 Human v16 microRNA 8×60K microarray slides; miRBase v16.0, cat no. G4870A) following the manufacturer's instructions v1.7. Briefly, one hundred nanograms of total RNA, from a working solution at 50 ng/μl in nuclease-free water, were used as input for each microarray experiment. Each slide contains 8 individual arrays, each array represents 1,349 microRNAs; 1205 human (mapped to 1194 miRNAs miRbase v20) and 144 viral.

The four key steps of the microarray process were:
1. Labelling of RNA with single-colour, Cy3-based reagent;
2. Hybridisation of the labelled RNA samples to the microarray;
3. Wash steps (*NB: the final wash after of the slides in pre-warmed Wash buffer 2 to 37° C. was carried out with the outer water bath at 45-50° C., rather than 37° C.); and
4. Slide scanning, data capture and feature extraction (matching array spots to miRNA IDs) and quality control checks on the resultant image and data files All microarray data passed Agilent quality control metrics ('good' to 'excellent'). Microarray data pre-processing and normalisation was then carried out with the AgiMicroRNA package in Bioconductor [details of which are described in López-Romero, P., 'Pre-processing and differential expression analysis of Agilent microRNA arrays using the AgiMicroRna Bioconductor library', BMC Genomics 12, 64 (2001) and Gentleman, R. C. et al., 'Bioconductor: open software development for computational biology and bioinformatics', Genome Biol. 5, R80 (2004)].

Array quality control was performed using outlier testing based on the following metrics:
average signal per array
average background per array
% present (% of miRNAs where expression is detected on each array)
data distributions per sample and pairwise Normalized miRNA expression levels of detected miRNAs (on the log 2 scale) were correlated with IDO-induction levels by correlation analysis using standard R/Bioconductor tools with Pearson's correlation ('cor.test') and false discovery multiple testing correction by the method described in Benjamini, Y. & Hochberg, 'Controlling the False Discovery Rate: A Practical and Powerful Approach to Multiple Testing', J R. Stat Soc B 57, 289-300 (1995).

Across the seven independent donors, the correlation analysis identified eight miRNAs for which their expression levels positively or negatively correlated with donor IDO-induction levels with correlation coefficients±>8.0. These are shown in Table 4 below:

TABLE 4

| miRNA ID | Correlation coefficient |
|---|---|
| hsa-miR-10b-5p | +0.89 |
| hsa-miR-136-5p | −0.88 |
| hsa-miR-140-3p | −0.84 |
| hsa-miR-23a-3p | −0.87 |
| hsa-miR-3651 | −0.81 |
| hsa-miR-491-3p | −0.89 |
| hsa-miR-574-3p | −0.93 |
| hsa-miR-574-5p | −0.85 |

FIGS. 1-8 show correlation plots expression levels vs IDO-induction for these miRNAs, demonstrating the correlation of these miRNA across the seven donors for levels of IDO induction.

Thus, a candidate group of eight miRNAs, the expression of which correlate with ±>0.8 correlation coefficient values, with MSC potential for IDO-induction, are identified. Of this candidate group of eight miRNAs, expression of one is positively correlated with IDO-induction, whilst the other seven are negatively correlated with IDO-induction, but in all cases with correlation coefficient values in excess of 0.8.

An assay for the screening of donor MSC populations to infer (or determine) IDO-induction potential (or relative induction potential as between MSCs of more than one donor) can be carried out using one or a panel of two or more of the identified eight candidate miRNAs and preferably up to six of the candidate miRNAs. These miRNAs could be selected and used to screen donor MSCs to predict and pre-select suitable donor cells with the highest immunosuppressive potential for further development as cell therapies.

Example 2—Migration Propensity of CD34+ Cells miRNA expression profiles from isolated human CD34+ cells from eight independent donors with different migration potentials were generated. These cell were then assayed in a SDF-1-based migration assay using standard methodologies and the percent migration determined. Correlation analysis was then carried out to identify miRNAs for which their expression correlated with and predicted the ability of the CD34+ cells to migrate towards a chemoattractant gradient.

Two candidate miRNAs were identified, the expression of which positively correlated with percent migration with a correlation coefficient±>0.8. These are shown in Table 5 below:

TABLE 5

| miRNA ID | Correlation coefficient |
|---|---|
| hsa-miR-1471 | +0.85 |
| hsa-miR-1288-3p | +0.93 |

Figure 9:
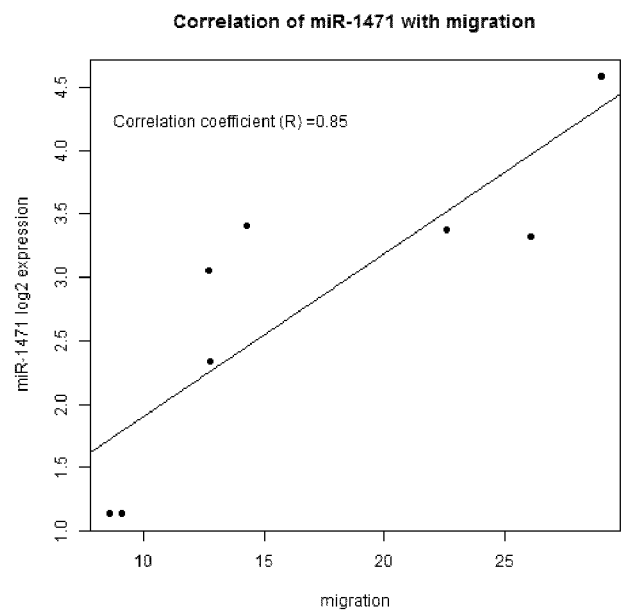
FIG. 9 is a correlation plot of miR-1471 expression levels vs percent migration for these miRNAs.
Figure 10:
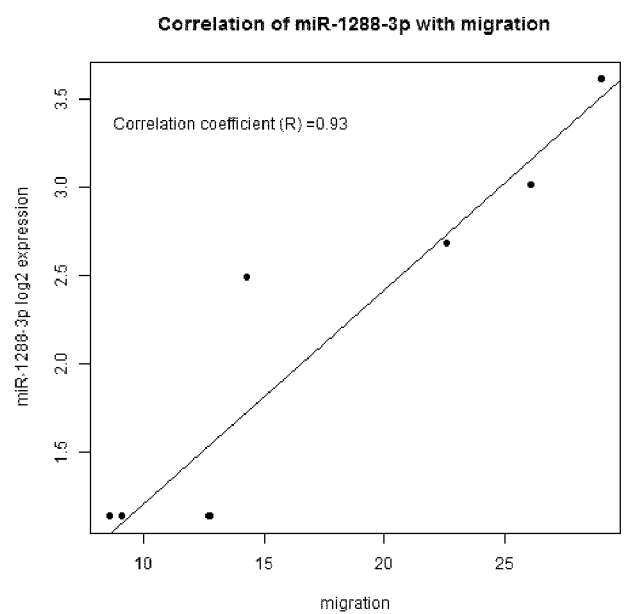
FIG. 10 is a correlation plot of miR-1288-3p expression levels vs percent migration for these miRNAs.

FIGS. 9 and 10 show correlation plots expression levels vs percent migration for these miRNAs.

Thus, the above-mentioned miRNAs can be used as basis for screening CD34+ cells or blood/bone marrow cell samples for propensity to migrate whereby the amount of cell material for expansion, the extent of expansion and/or the dose of cells for administration in autologous cell therapy.

The invention has been described with reference to a preferred embodiment. However, it will be appreciated that variations and modifications can be effected by a person of ordinary skill in the art without departing from the scope of the invention.

The invention claimed is:

1. A method of screening a population of mesenchymal stem cells (MSCs) from a donor or different donors for a propensity for indoleamine-2,3-dioxygenase (IDO) induction by interferon-gamma (IFN-γ), the method comprising:
    assaying the MSCs against a pre-determined miRNA or panel of miRNAs known or determined to correlate with the IDO induction by IFN-γ;
    generating non-coding RNA expression data for the assayed miRNA or panel of miRNAs and from the miRNA expression data;
    identifying, determining or inferring a propensity for the IDO induction by IFN-γ.

2. The method as claimed in claim 1, wherein the identifying, determining or inferring a propensity is by comparing the expression data from the assay with expression levels, trends or patterns known to be associated with IDO induction by IFN-γ.

3. The method as claimed in claim 1, which is by assaying the MSCs against the predetermined miRNA or panel of miRNAs.

4. The method as claimed in claim 1, wherein the panel of miRNAs comprises at least two non-coding RNA.

5. The method as claimed in claim 4, wherein at least one miRNA is positively correlated and at least one miRNA is negatively correlated with the IDO induction by IFN-γ.

6. The method as claimed in claim 1, wherein the the screening is for a purpose is selected from the group consisting of: a bioprocess application, a cell therapy application, patient stratification for cell therapy, cell growth and donor selection.

7. The method as claimed in claim 1, wherein the screening is for a cellular functional effect selected from the group consisting of: an effect on an applied cell population by a tissue to which it is applied, an effect on a tissue to which a cell population is applied, production of paracrine factors, proliferation activity, differentiation tendency, engraftment potential, immunosuppressive activity, migration potential, response to activity inducing agents or response to assays.

8. The method as claimed in claim 1, which further comprises making a selection or treatment decision based upon the identification, determination or inference of propensity for the IDO induction by IFN-γ.

9. The method of claim 1 wherein the MSCs are from the single donor.

10. The method of claim 1 wherein the MSCs are from the different donors.

11. The method of claim 1 further comprising screening a second population of mesenchymal stem cells (MSCs) from the donor or the different donors for the propensity for the indoleamine-2,3-dioxygenase (IDO) induction by IFN-γ.

* * * * *